United States Patent
Vaz et al.

(10) Patent No.: US 11,963,815 B2
(45) Date of Patent: *Apr. 23, 2024

(54) METHODS AND SYSTEMS FOR AN ADAPTIVE CONTRAST SCAN

(71) Applicant: GE Precision Healthcare LLC, Milwaukee, WI (US)

(72) Inventors: Michael Sarju Vaz, Milwaukee, WI (US); Maud Bonnard, Brookfield, WI (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 583 days.

This patent is subject to a terminal disclaimer.

(21) Appl. No.: 17/010,674

(22) Filed: Sep. 2, 2020

(65) Prior Publication Data

US 2022/0061793 A1 Mar. 3, 2022

(51) Int. Cl.
*A61B 6/00* (2006.01)
*A61B 6/50* (2024.01)
*G06N 20/00* (2019.01)

(52) U.S. Cl.
CPC ........... *A61B 6/545* (2013.01); *A61B 6/481* (2013.01); *A61B 6/507* (2013.01); *A61B 6/5217* (2013.01); *G06N 20/00* (2019.01)

(58) Field of Classification Search
CPC ....... A61B 6/032; A61B 6/037; A61B 6/4241; A61B 6/461; A61B 6/465; A61B 6/467; A61B 6/468; A61B 6/469; A61B 6/481; A61B 6/482; A61B 6/501; A61B 6/504; A61B 6/507; A61B 6/5217; A61B 6/54;

(Continued)

(56) References Cited

U.S. PATENT DOCUMENTS

| | | | |
|---|---|---|---|
| 5,400,378 A | 3/1995 | Toth | |
| 6,023,494 A | 2/2000 | Senzig et al. | |
| 6,236,706 B1 | 5/2001 | Hsieh | |

(Continued)

FOREIGN PATENT DOCUMENTS

CN 101277648 A 10/2008

OTHER PUBLICATIONS

Hinzpeter, R. et al., "CT Angiography of the Aorta: Contrast Timing by Using a Fixed versus a Patient-specific Trigger Delay," Radiology, vol. 291, No. 2, May 2019, 8 pages.

(Continued)

*Primary Examiner* — Michael T Rozanski
(74) *Attorney, Agent, or Firm* — McCoy Russell LLP

(57) ABSTRACT

Methods and systems are provided for adaptive scan control. In one embodiment, a method for an imaging system includes performing, with the imaging system, a first contrast scan of a subject including injection of a contrast agent to the subject; processing projection data of the subject acquired during the first contrast scan to measure a contrast signal of the subject at a monitoring area; estimating a target acquisition timing for a first acquisition of a second contrast scan of the subject based on the contrast signal; and performing, with the imaging system, the second contrast scan of the subject, with the first acquisition performed at the target acquisition timing and without performing any monitoring scans between the first contrast scan and the second contrast scan.

20 Claims, 13 Drawing Sheets

(58) Field of Classification Search
CPC ........ A61B 6/542; A61B 6/545; G06N 20/00; G06N 3/04
See application file for complete search history.

(56) References Cited

U.S. PATENT DOCUMENTS

| | | | |
|---|---|---|---|
| 6,256,368 | B1 | 7/2001 | Hsieh et al. |
| 6,891,918 | B2 | 5/2005 | Drummond et al. |
| 7,145,982 | B2 | 12/2006 | Ikeda et al. |
| 7,983,460 | B2 | 7/2011 | Licato et al. |
| 9,327,143 | B2 | 5/2016 | Gillece et al. |
| 9,486,176 | B2 | 11/2016 | Goyal |
| 9,517,042 | B2 | 12/2016 | Hsieh et al. |
| 9,622,717 | B2 | 4/2017 | Londt et al. |
| 10,349,909 | B2 | 7/2019 | Okerlund et al. |
| 11,179,127 | B2 * | 11/2021 | Vaz ................. A61B 6/507 |
| 11,523,792 | B2 * | 12/2022 | Forbes ............. A61B 6/545 |
| 2017/0086772 | A1 | 3/2017 | Vaz et al. |
| 2017/0209113 | A1 | 7/2017 | Jackson et al. |
| 2018/0049714 | A1 | 2/2018 | Nett |
| 2019/0231288 | A1 | 8/2019 | Profio et al. |

OTHER PUBLICATIONS

Lewis, C. et al., "Methods and Systems for Protocol Management," U.S. Appl. No. 16/553,028, filed Aug. 27, 2019, 59 pages.
Vaz, M. et al., "Methods and Systems for Timing a Second Contrast Bolus," U.S. Appl. No. 16/672,261, filed Nov. 1, 2019, 84 pages.
Vaz, M. et al., "Methods and Systems for an Adaptive Multi-Phase Angiography Scan," U.S. Appl. No. 16/672,281, filed Nov. 1, 2019, 85 pages.
Vaz, M. et al., "Methods and Systems for an Adaptive Five-Zone Perfusion Scan," U.S. Appl. No. 16/672,314, filed Nov. 1, 2019, 85 pages.
Vaz, M. et al., "Methods and Systems for a Single-Bolus Angiography and Perfusion Scan," U.S. Appl. No. 16/672,336, filed Nov. 1, 2019, 85 pages.
Vaz, M. et al., "Methods and Systems for an Adaptive Four-Zone Perfusion Scan," U.S. Appl. No. 16/672,350, filed Nov. 1, 2019, 85 pages.

* cited by examiner

First Contrast Scan Series (a.k.a. "Contrast Scan #1")

Scan Series Name: CTP

Injection #1 Protocol: 350 mg/mL | 40 mL | 4 mL/s

Second Contrast Scan Series (a.k.a. "Contrast Scan #2")

Scan Series Name: CTA

Injection #2 Protocol: 350 mg/mL | 40-70 mL | 4 mL/s

○ Auto-optimize start time of injection #2 for the individual patient

○ Simplify CTA (i.e. bypass Smart Prep and use CTP as Virtual Timing Bolus)

Fixed Timing for Injection #2 Start: 180 seconds after Inj #1 End

Preview: Desired timing for Simplified CTA Acquisition

Auto Adaptive Prep Delay: TBD s — Arterial Peak, Tissue Peak, Venous Peak

Rx: Simplified Head & Neck CTA

| | Initialize: Fallback | Desired Rx: No SP & lower contrast load |
|---|---|---|
| Smart Prep | Enable SP | Skip SP |
| Adaptive Prep Delay | No --> Do Fixed | Yes --> Do Adaptive PD |
| Contrast Volume | 70 mL | ○ Same as CTP  40 mL |

○ Match table speed with contrast travel time between scan Start/End locations

Adapt: Rotation Time (and mA to keep mAs fixed) to control table speed

FIG. 13

METHODS AND SYSTEMS FOR AN ADAPTIVE CONTRAST SCAN

FIELD

Embodiments of the subject matter disclosed herein relate to non-invasive diagnostic imaging, and more particularly, to real-time adaptive contrast imaging.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

For emergency room (ER) stroke management, time is critical to determine a proper course of treatment. For every minute a large vessel ischemic stroke is untreated, the average patient loses 1.9 million neurons. For each hour in which a treatment fails, the patient loses as many neurons as it does in almost 3.6 years of normal aging. Current standards of care may include a CT angiography (CTA) study to detect the presence of a large vessel occlusion (LVO) and the path to reach that LVO with a catheter to perform a thrombectomy. Prior to performing the CTA study, typical methods include a series of monitoring scans where contrast levels in the patient are monitored in order to generate a CTA scan prescription personalized to the patient. However, these monitoring scans delay the start of the CTA scan, thus delaying diagnosis and treatment. Further, the monitoring scans may disrupt other non-acquisition functions the CT system may be performing, such as background reconstruction of images from data acquired during a prior CT scan.

BRIEF DESCRIPTION

In one embodiment, a method for an imaging system includes performing, with the imaging system, a first contrast scan of a subject including injection of a contrast agent to the subject; processing projection data of the subject acquired during the first contrast scan to measure a contrast signal of the subject at a monitoring area; estimating a target acquisition timing for a first acquisition of a second contrast scan of the subject based on the contrast signal; and performing, with the imaging system, the second contrast scan of the subject, with the first acquisition performed at the target acquisition timing and without performing any monitoring scans between the first contrast scan and the second contrast scan.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 13 shows an example adaptive scan protocol GUI according to an embodiment of the disclosure;

DETAILED DESCRIPTION

Figure 1:
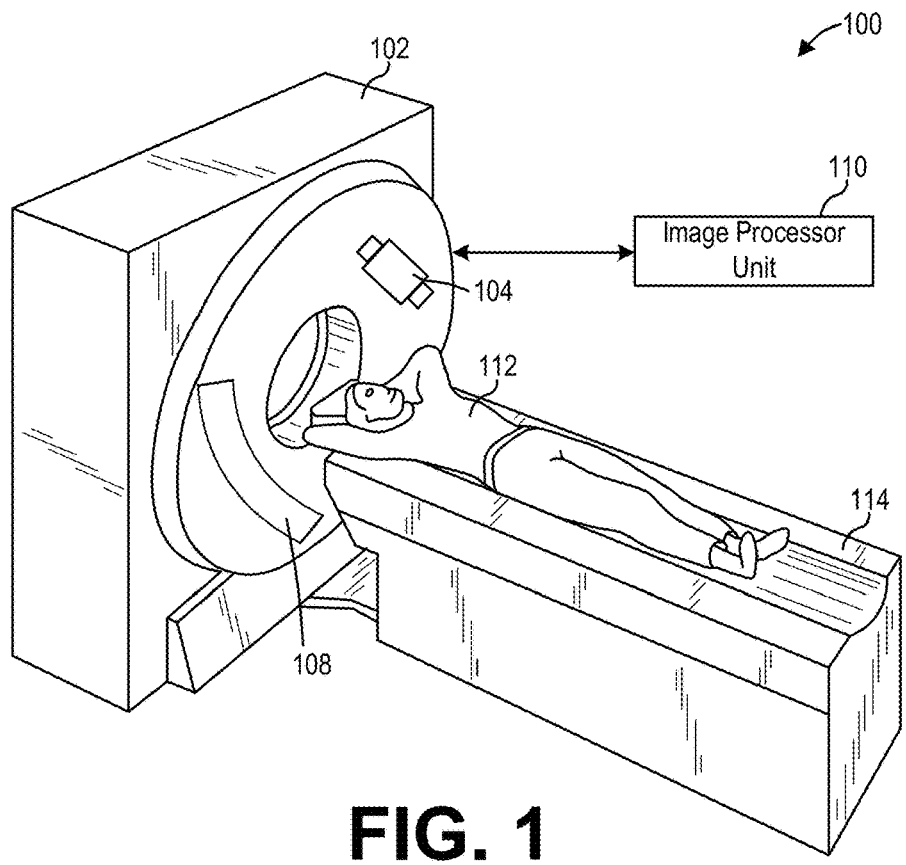
FIG. 1 shows a pictorial view of an imaging system, according to an embodiment.

Some diagnostic imaging protocols, such as protocols to diagnose acute stroke in a patient, include one or more contrast scans, where a contrast agent is administered to the patient prior to the diagnostic imaging scan. Example contrast scans include a computed tomography (CT) angiography (CTA) scan and a CT perfusion (CTP) scan. CTP and CTA scans, when used during acute stroke care, may be used by clinicians as a tool to decide if a particular patient will benefit from endovascular thrombectomy. Due to the time sensitive nature of acute stroke care and the acquisition and reconstruction duration of CTP and CTA scans, the CTP and CTA scans may be performed as soon as a patient arrives at a medical facility, before patient information and any recent patient hemodynamic information is available. Thus, the onset of each scan may be delayed as a short segment of the patient's hemodynamic information is analyzed via a series of monitoring scans, in order to set personalized scan prescriptions that may reduce the likelihood that the scans may need to be repeated.

In addition to extending the overall amount of time the CTP and CTA scans last, these monitoring scans may result in a relatively large amount of contrast agent having to be injected, particularly when a CTA scan and a CTP scan are performed on the same patient in rapid succession. For example, a respective bolus of contrast agent may be injected prior to each contrast scan, in an amount sufficient to ensure contrast is present when the enhancement is detected, through the table backing up and table acceleration, and for the actual diagnostic acquisitions. For some patients (e.g., patients with kidney issues, such as patients who have recently undergone a kidney replacement), these large contrast agent injections may be problematic, and thus only one contrast scan may be performed in order to reduce the contrast agent load for the patient.

Further, many scan protocols may dictate that a CTA scan be performed after a CTP scan, which may shorten the amount of time for both scans to be conducted by performing some tasks in parallel. For example, during the CTA scan, the data acquired during the CTP scan may be processed and reconstructed into one or more images. However, the monitoring scans performed as part of the CTA scan may be processing intensive and thus disrupt the CTP image reconstruction process, thereby delaying when the final CTP images/perfusion maps are ready for analysis.

Thus, as will be described in more detail below, a personalized, adaptive CTA scan of a patient may be performed using the patient's contrast kinetics determined during a prior contrast scan (such as a CTP scan performed immediately before the CTA scan). The adaptive CTA scan described herein may adjust when one or more acquisitions of the CTA scan are performed based on the patient's individual contrast agent kinetics, such as the amount of time from contrast agent injection until various inflection points/time points of interest on the patient's arterial inflow function (AIF) curve and/or venous outflow function (VOF) curve at the aortic arch are reached. To determine the patient's individual contrast agent kinetics, a contrast agent signal may be measured during the CTP scan, which may comprise a measured contrast level in a monitoring region of the patient (e.g., the brain of the patient). This contrast agent signal may be entered as input to a machine learning (ML) model that may output an estimated AIF curve and an estimated VOF curve for the monitoring region (and/or time points of interest from the AIF and VOF curves, such as an arterial peak, a venous peak, and/or a venous return to baseline). Based on the output of the ML model, the arterial peak (or other time points of interest) at the aortic arch may be determined, and the first (neck) CTA acquisition may commence at the determined time of the arterial peak at the aortic arch following a second contrast agent injection. Additionally, the duration of the second contrast agent injection may be adjusted to a minimum time based on a determined scan range (e.g., from the base of the patient's neck to the patient's head), an estimated amount of time for the contrast agent arterial peak to move from the neck to the head, and other parameters. In doing so, patient x-ray radiation dose and contrast agent load may be reduced, a reconstruction computation load may be reduced, and/or a scan duration may be shortened while still acquiring high quality diagnostic images to support patient diagnosis.

However, in some patients, it may be challenging to identify the estimated AIF curve and the estimated VOF curve (and/or time points of interest from the AIF and VOF curves), as some patients may exhibit contrast agent kinetics that cannot be associated (e.g., by the ML model) with specific AIF and/or VOF curves in a time frame under which such protocol adaptation may be beneficial. Thus, the scan prescription described herein may start out as a fallback, worst case scenario scan prescription that may dictate monitoring scans be performed for the CTA scan so that quality diagnostic images for all patients may be obtained even if the estimated contrast enhancement curves cannot be determined. Then, if the contrast enhancement curves can be estimated, the fallback scan prescription may be adapted on the fly to omit the monitoring scans, as described herein.

Figure 2:
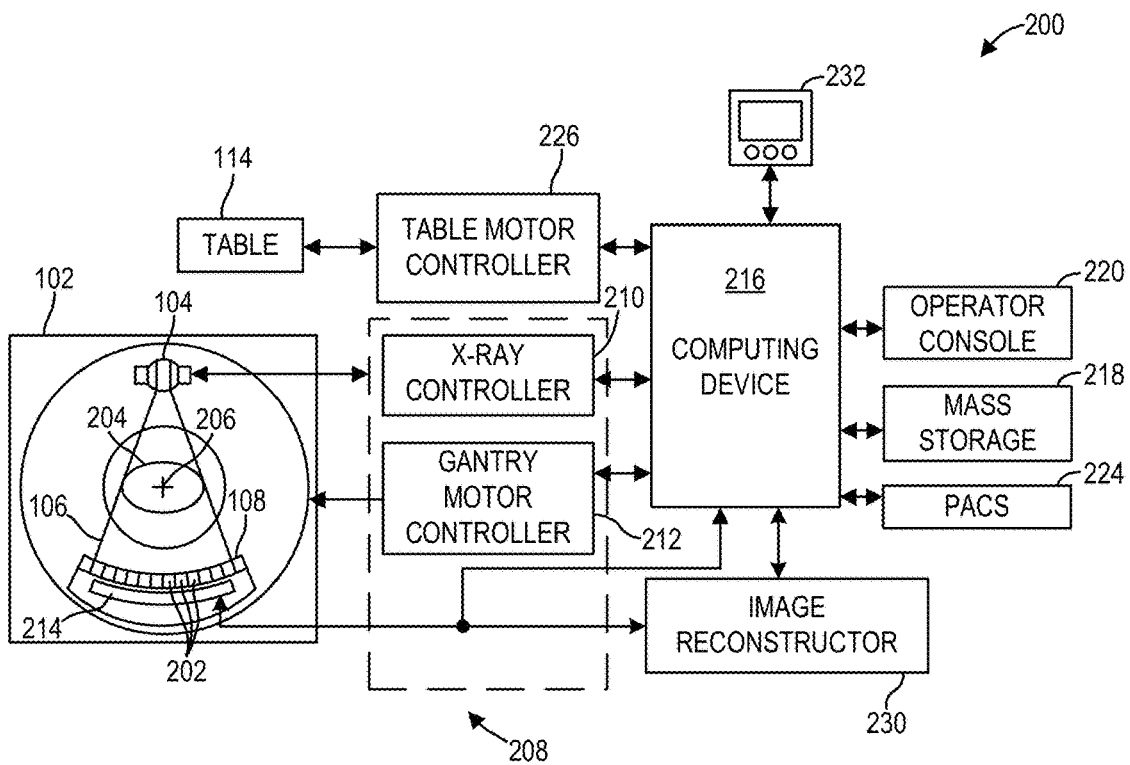
FIG. 2 shows a block schematic diagram of an exemplary imaging system, according to an embodiment.
Figure 3:
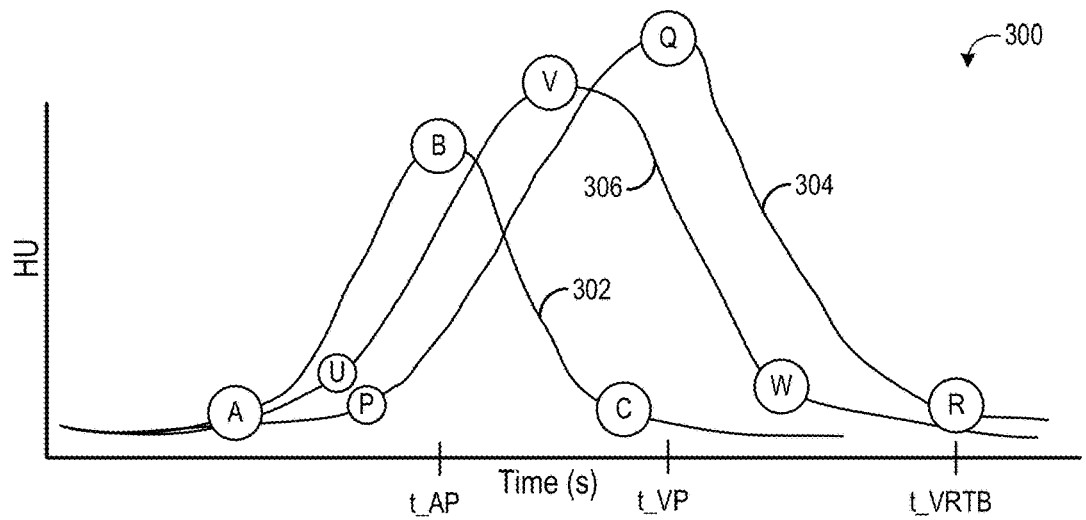
FIG. 3 shows a graph illustrating an example arterial inflow function (AIF) curve, an example a venous outflow function (VOF) curve, and an example tissue uptake curve (TUC) generated during a contrast scan.
Figure 4:
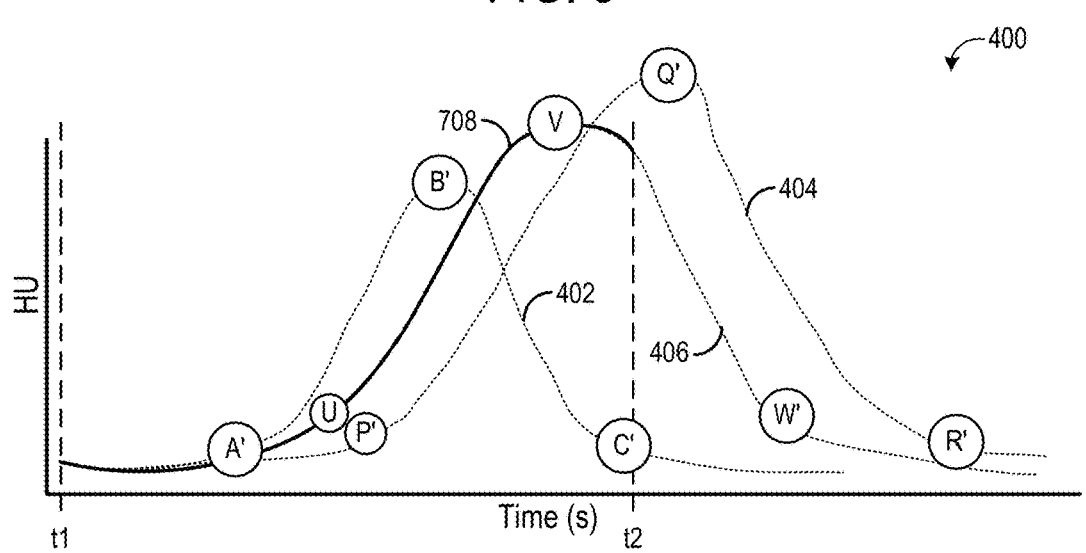
FIG. 4 shows a graph illustrating an estimated AIF curve, an estimated VOF curve, and an estimated TUC generated according to an embodiment of the disclosure.
Figure 5:
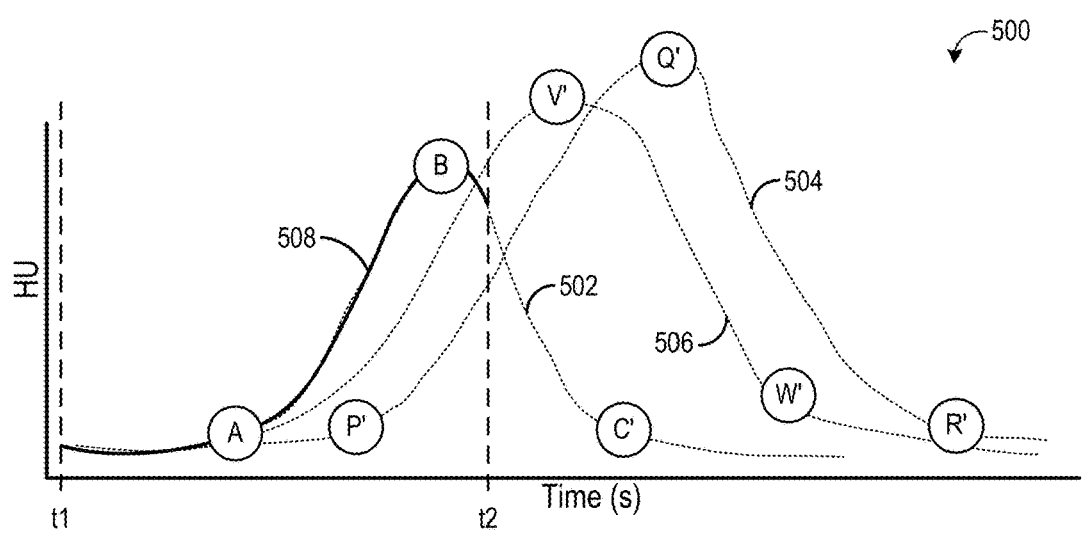
FIG. 5 shows a graph illustrating an estimated AIF curve, an estimated VOF curve, and an estimated TUC generated according to another embodiment of the disclosure.
Figure 7A:
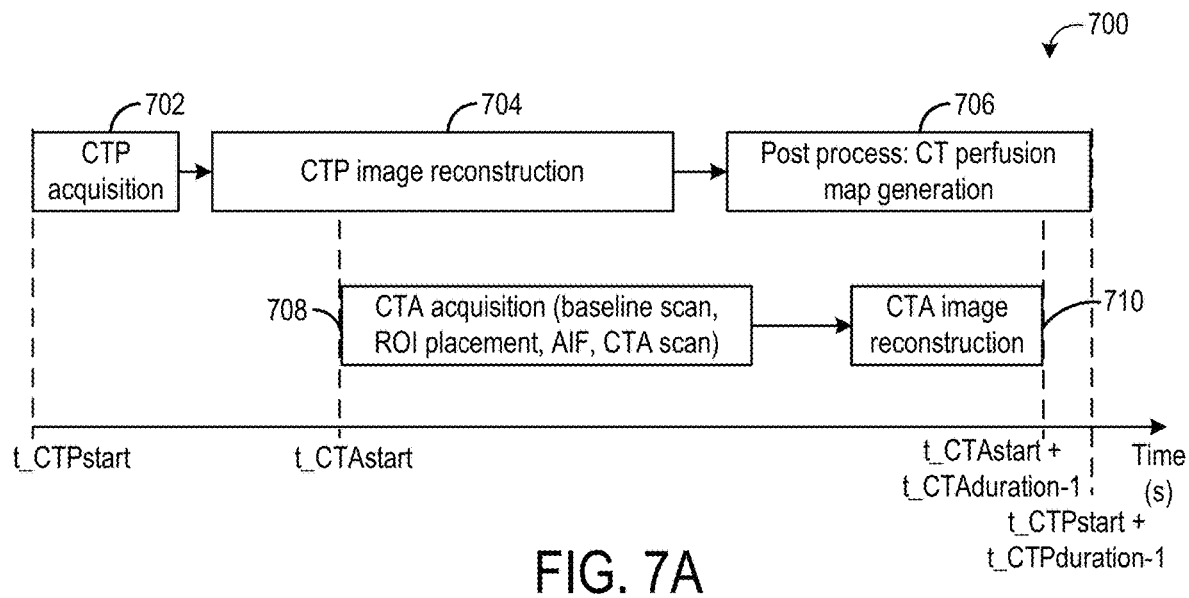
FIG. 7A is a timeline showing the stages of a perfusion scan followed by an angiography scan, where the angiography scan includes monitoring scans.
Figure 7B:
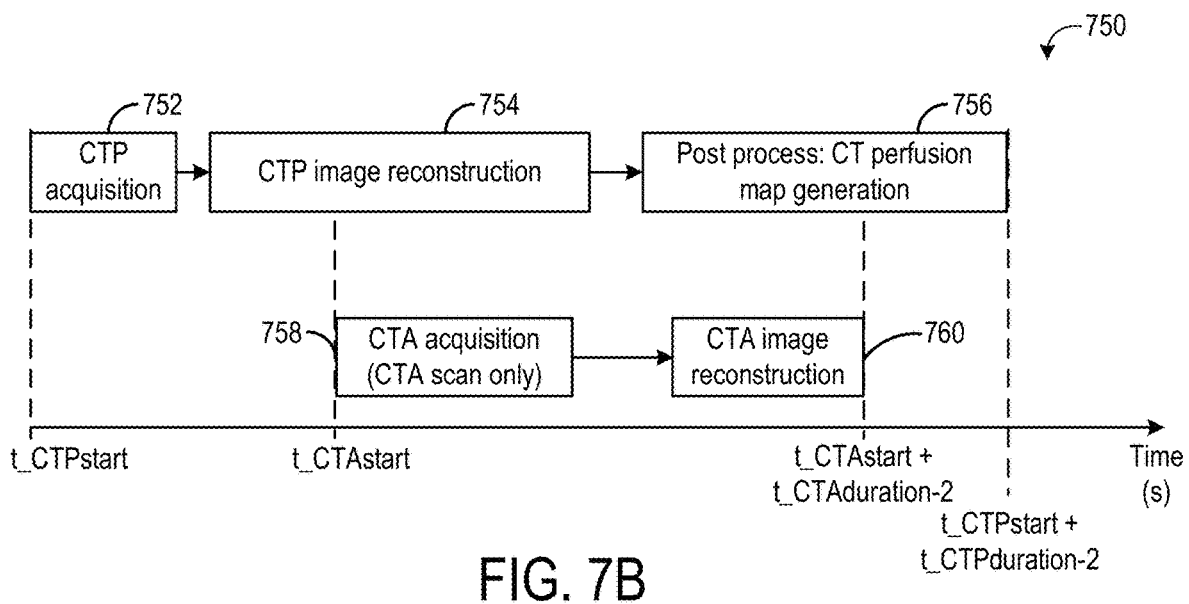
FIG. 7B is a timeline showing the stages of a perfusion scan followed an adaptive angiography scan according to the disclosure.
Figure 8:
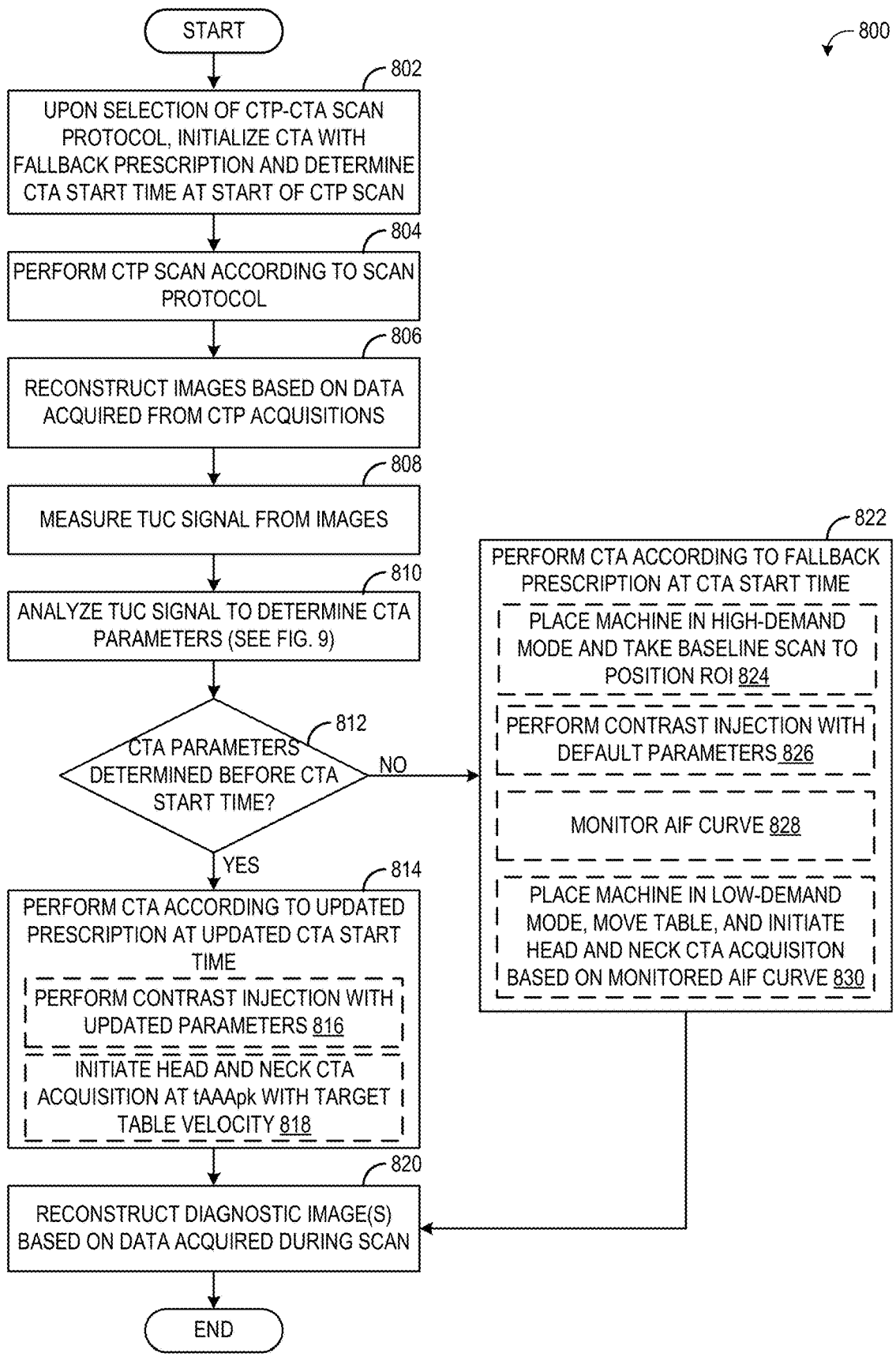
FIG. 8 is a flowchart illustrating a method for performing an adaptive angiography scan including a default fallback scan prescription, according to an embodiment of the disclosure.
Figure 9:
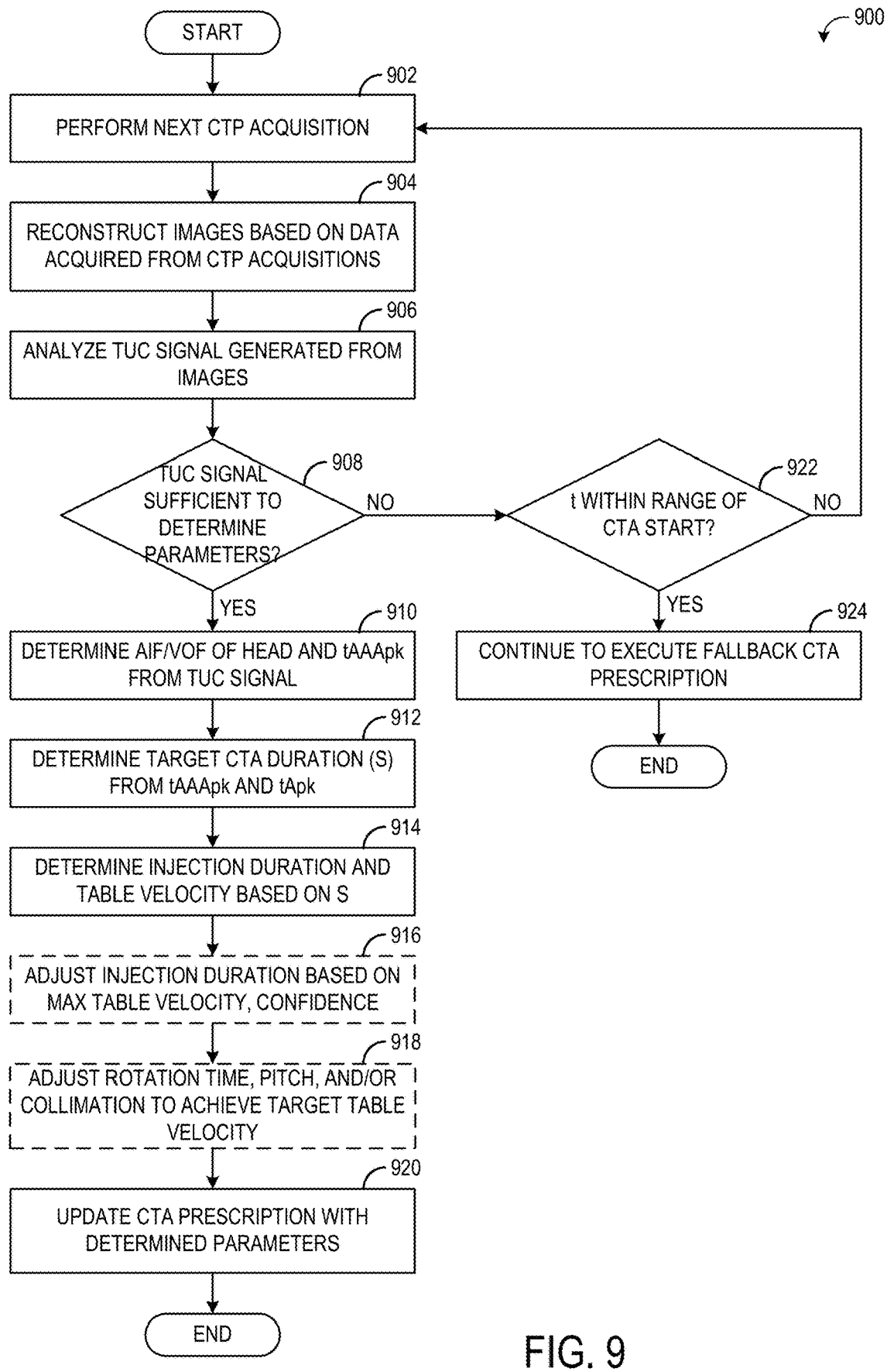
FIG. 9 is a flowchart illustrating a method for determining angiography scan parameters based on contrast kinetics from a prior scan, according to an embodiment of the disclosure.
Figure 10:
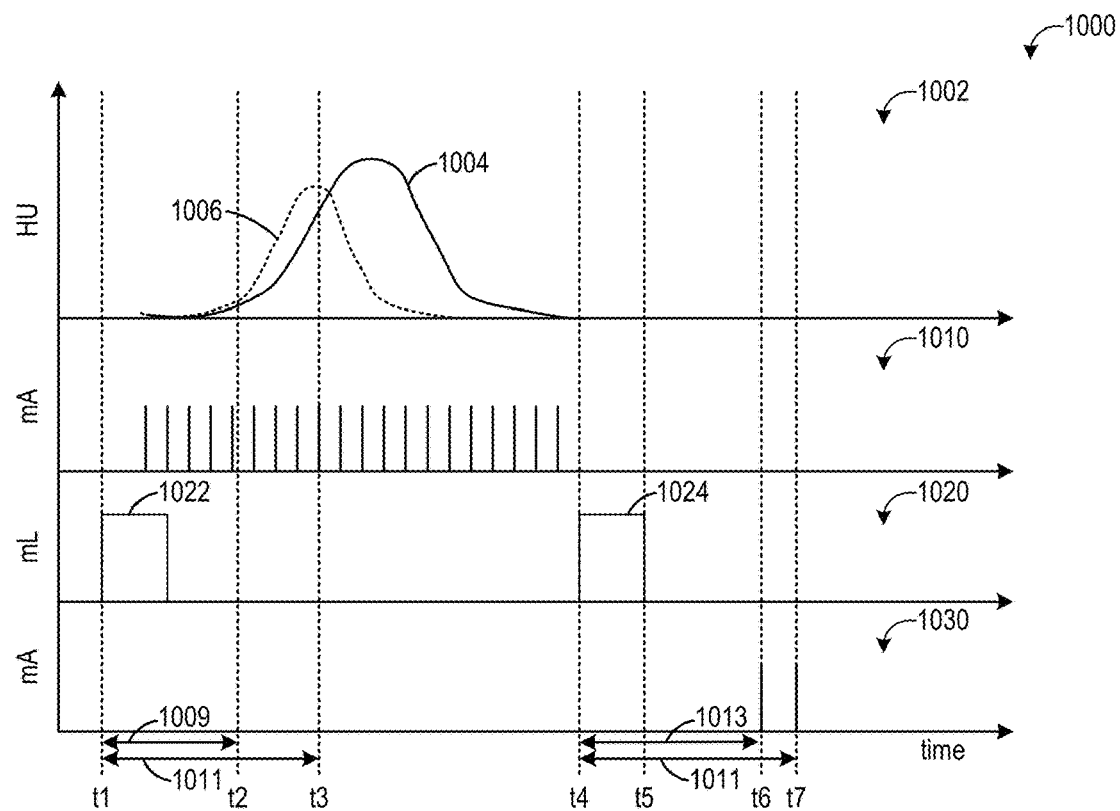
FIG. 10 is a set of graphs depicting a perfusion scan prescription and an adapted angiography scan prescription, the adapted perfusion scan prescription adapted based on perfusion kinetics determined for a first patient.
Figure 11:
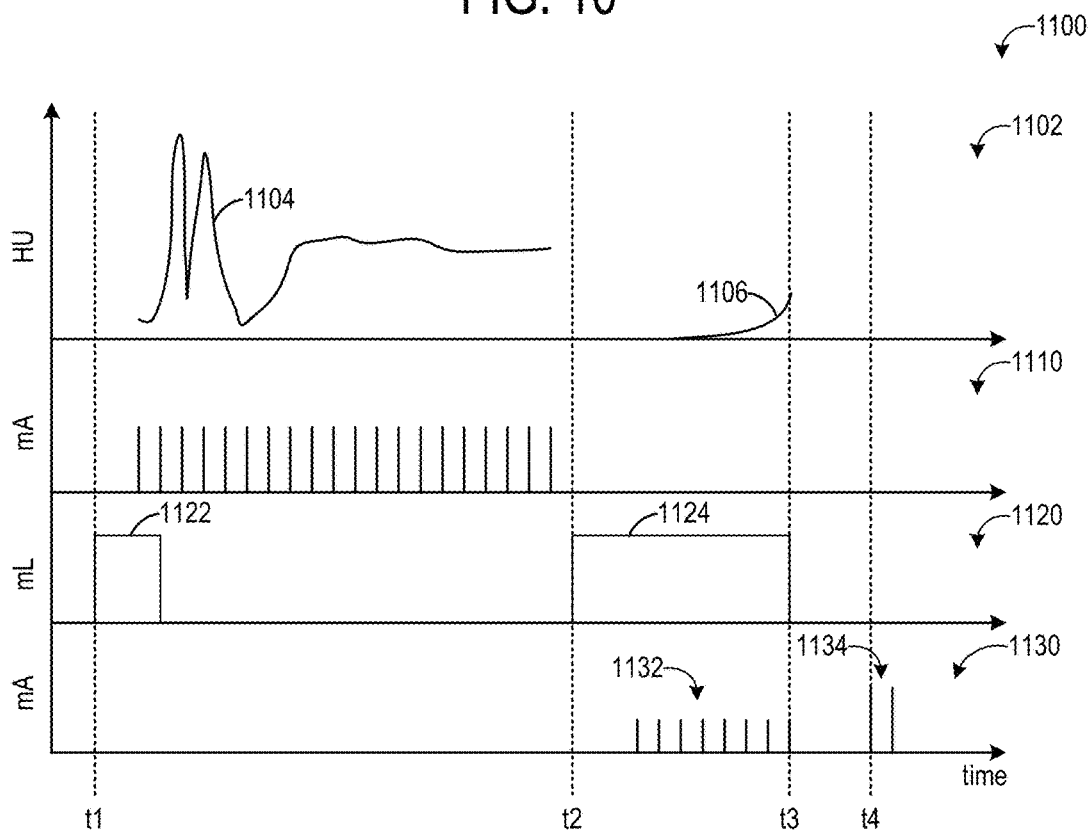
FIG. 11 is a set of graphs depicting a perfusion scan prescription and a fallback angiography scan prescription for a second patient.

An example of a computed tomography (CT) imaging system that may be used to perform the contrast scans in accordance with the present techniques is provided in FIGS. 1 and 2. As described above, the adaptation of the contrast scans may be dependent on the AIF and/or VOF curves of the contrast agent, which vary from patient to patient. FIG. 3 shows example AIF and VOF curves for a patient. A portion of the AIF curve may be directly measured prior to a first contrast scan commencing or during the first portion of the first contrast scan, and this portion may be used as input to a model to estimate the remaining AIF curve and the VOF curve for the patient, as shown in FIG. 5. As another example, rather than measuring the AIF, tissue uptake of the contrast agent may be measured for a duration, and this measured portion of the tissue uptake curve (TUC) may be entered into a model to estimate the AIF and VOF curves, as shown in FIG. 4. Adaptive scan control may be carried out according to the method of FIGS. 6A and 6B, where individual patient contrast agent kinetics as determined from a prior scan, such as the TUC during a CTP scan, may be used to set the scan prescription of a CTA scan. FIGS. 7A and 7B show overlapping stages of a CTP scan and a CTA scan, where the CTA scan is not adapted (FIG. 7A) and where the CTA scan is adapted (FIG. 7B). If contrast agent kinetics cannot be reliably determined, a fallback scan prescription may be followed for the CTA scan, otherwise the fallback scan prescription may be adapted, as shown by FIGS. 8-9. FIG. 10 shows an example scan prescription adaptation for a first patient, while FIG. 11 shows an example patient where the fallback scan prescription is not adapted.

Figure 12:
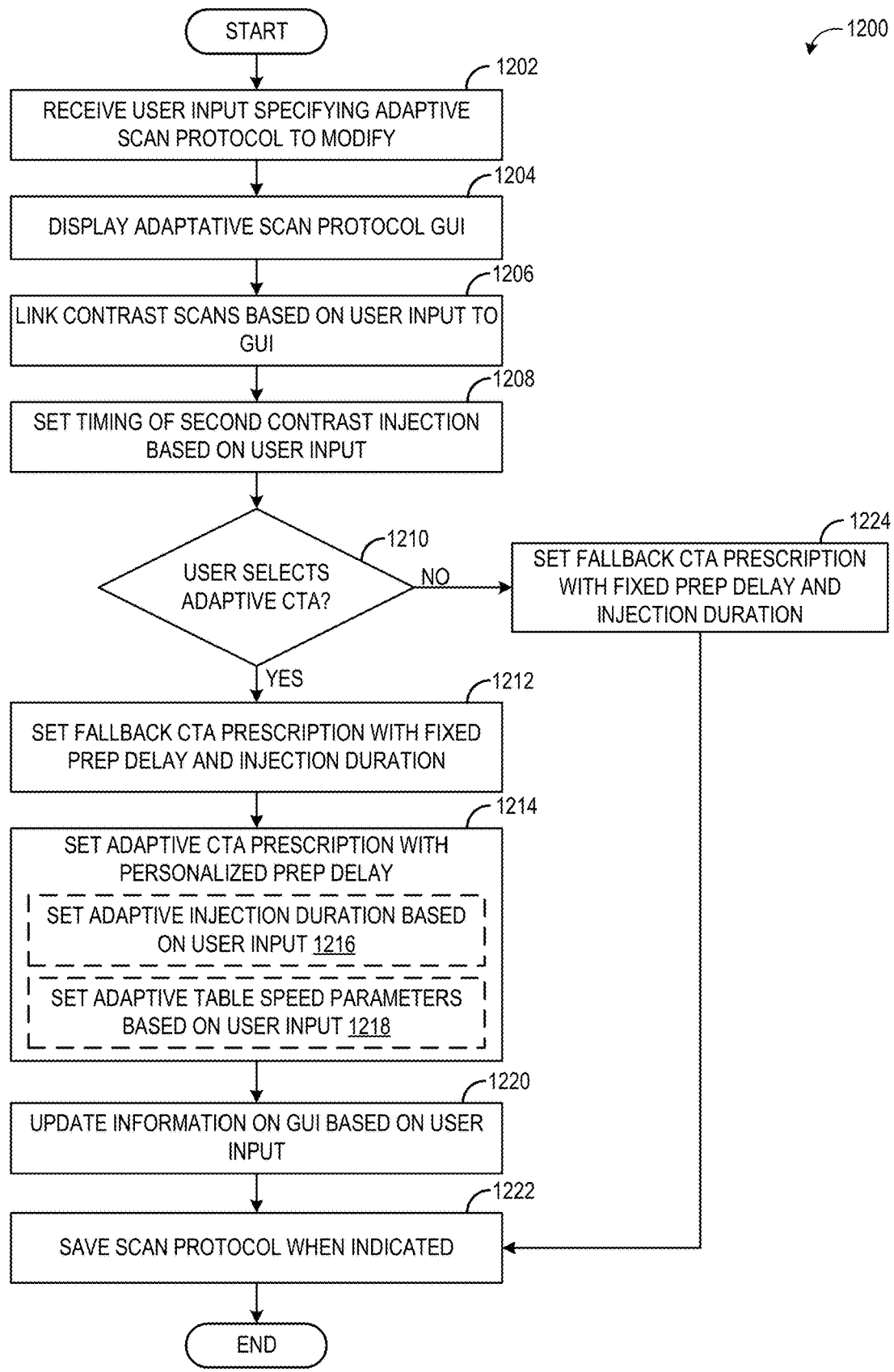
FIG. 12 is a flow chart illustrating a method for setting an adaptive scan protocol via an adaptive scan protocol graphical user interface (GUI), according to an embodiment of the disclosure.
Figure 14:
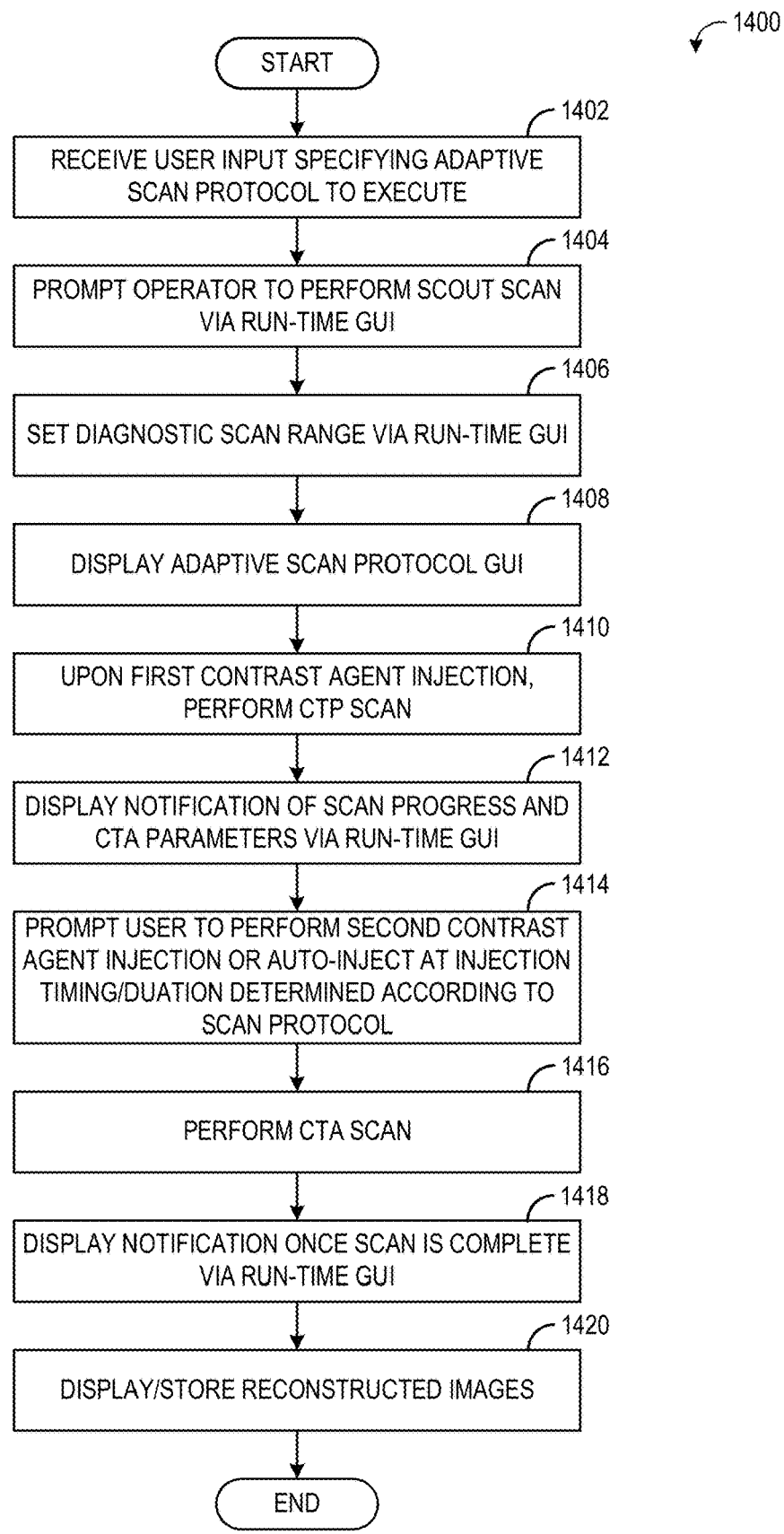
FIG. 14 is a flow chart illustrating a method for executing an adaptive scan protocol via a run-time GUI, according to an embodiment of the disclosure.
Figure 15:
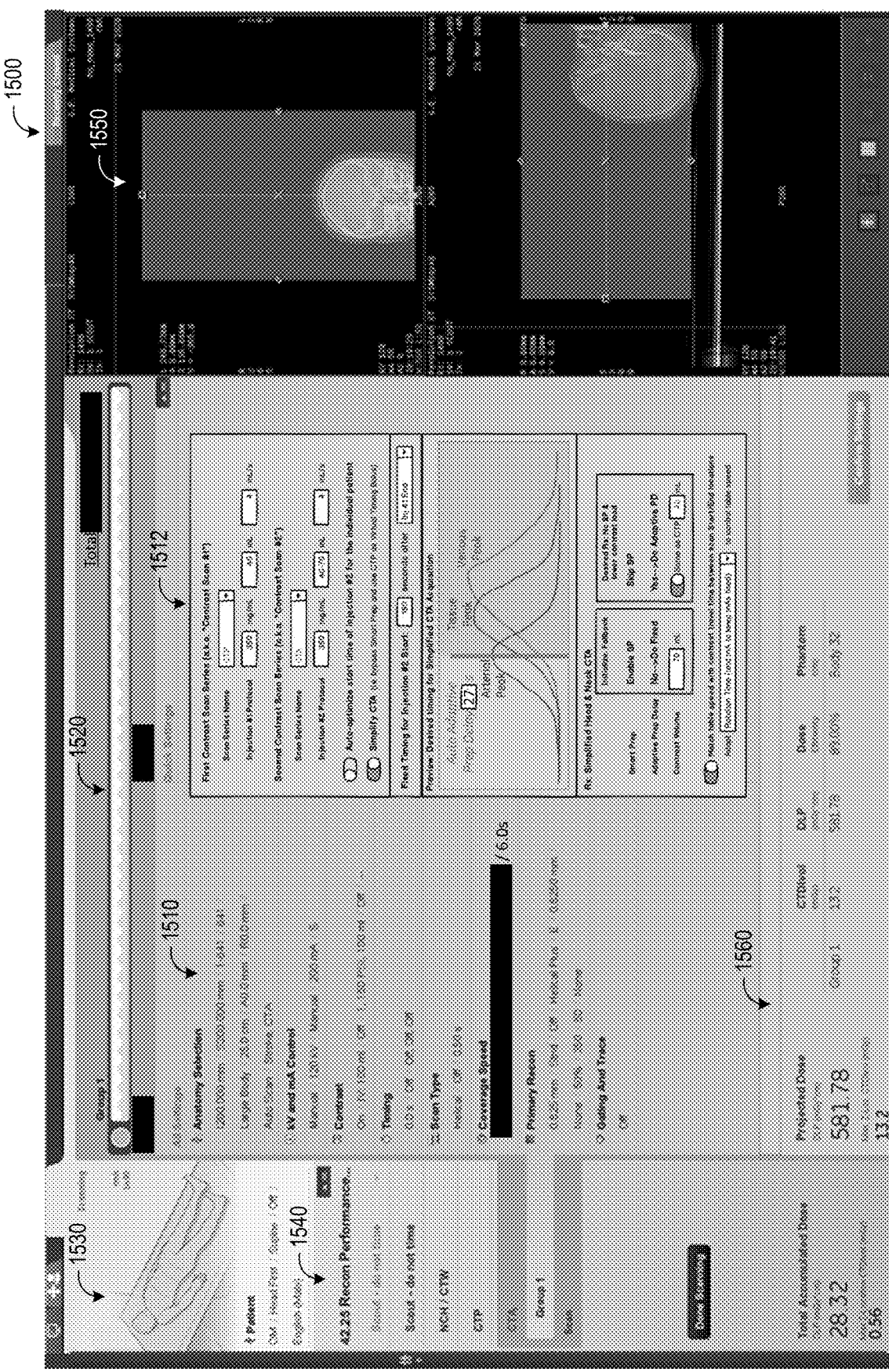
FIG. 15 shows an example run-time GUI, according to an embodiment of the disclosure.
Figure 16:
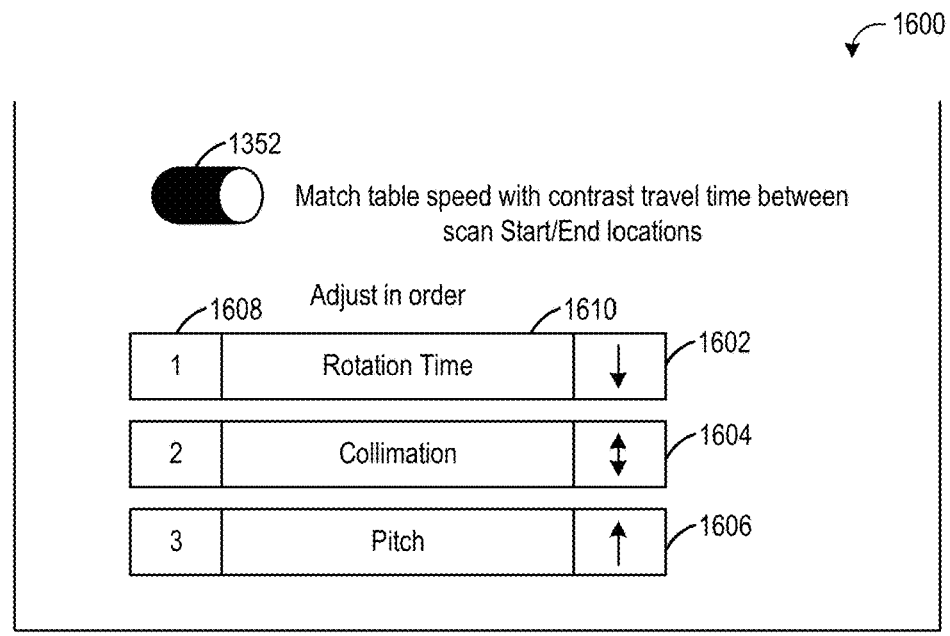
FIG. 16 shows a first example portion of an adaptive scan protocol GUI.
Figure 17:
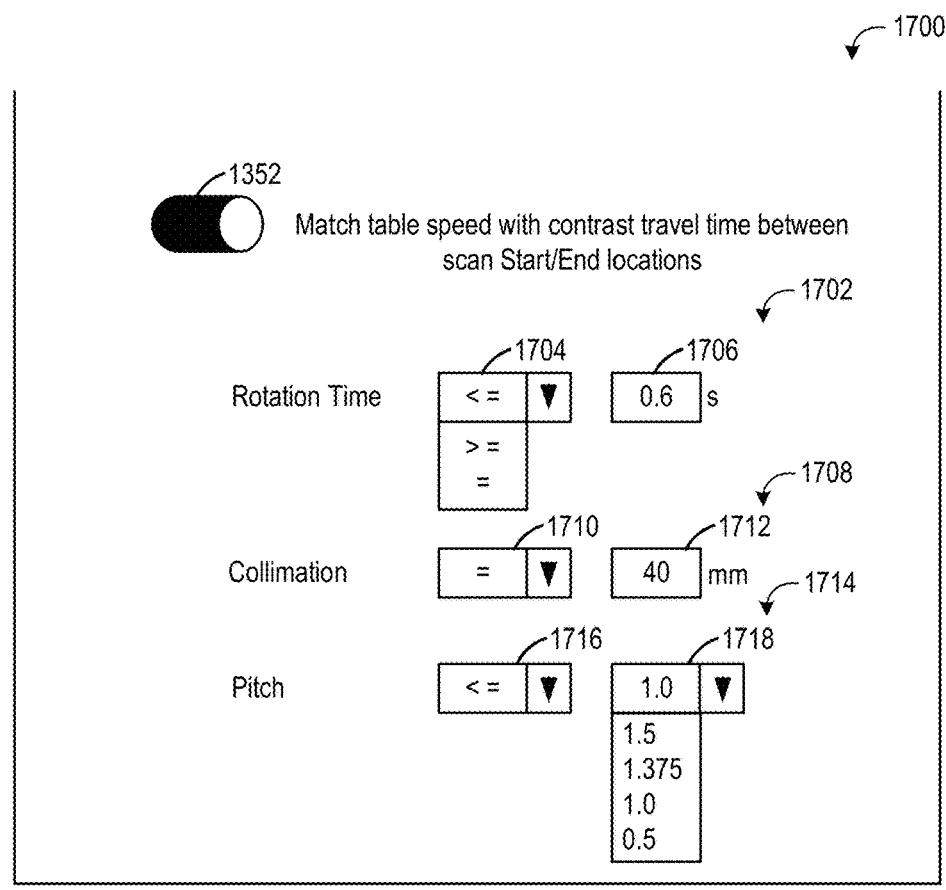
FIG. 17 shows a second example portion of an adaptive scan protocol GUI.

Parameters of the fallback scan prescription and the adaptive scan prescription for the CTA described above may be specified in advance according to an adaptive scan protocol defined by a lead technologist or other authorized user via input to an adaptive scan protocol graphical user interface (GUI). Then, during execution of the adaptive scan protocol by a scanning technologist or other imaging system operator, the fallback and adaptive prescriptions may be loaded and determined automatically, without requiring additional input from the scanning technologist. In doing so, the cognitive load placed on the scanning technologist at the time of scanning may be reduced, which may speed up the process of scanning the patient and reduce scanning errors. FIG. 12 shows a method for setting an adaptive scan protocol and FIG. 13 shows an example adaptive scan protocol GUI. The adaptive scan protocol GUI may include a section via which adaptation to certain CTA parameters may be specified in order to match table velocity with contrast travel time, further examples of which are shown in FIGS. 16 and 17. FIG. 14 shows a method for executing an adaptive scan protocol, which may include user interaction with a run-time GUI, an example of which is shown in FIG. 15.

Though a CT system is described by way of example, it should be understood that the present techniques may also be useful when applied to images acquired using other imaging modalities, such as x-ray imaging systems, magnetic resonance imaging (MRI) systems, positron emission tomography (PET) imaging systems, single-photon emission computed tomography (SPECT) imaging systems, ultrasound imaging systems, and combinations thereof (e.g., multi-modality imaging systems, such as PET/CT, PET/MR or SPECT/CT imaging systems). The present discussion of a CT imaging modality is provided merely as an example of one suitable imaging modality. Further, while the present techniques may be discussed herein with respect to head/neck scans such as acute stroke scan protocols, the present techniques may be applied during other contrast scan protocols, such as cardiac scans, liver scans, etc.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 (see FIG. 2) for use in imaging the subject 112 laying on a table 114. Specifically, the x-ray source 104 is configured to project the x-ray radiation beams 106 towards a detector array 108 positioned on the opposite side of the gantry 102. Although FIG. 1 depicts only a single x-ray source 104, in certain embodiments, multiple x-ray sources and detectors may be employed to project a plurality of x-ray radiation beams 106 for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector element of the array produces a separate electrical signal that is a measurement of the x-ray beam attenuation at the detector location. The attenuation measurements from all the detector elements are acquired separately to produce a transmission profile.

In some CT systems, the x-ray source and the detector array are rotated with a gantry within the imaging plane and around the object to be imaged such that an angle at which the radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes (such as the methods described below with reference to FIGS. 6, 8, and 9) described further herein may be stored as executable instructions in non-transitory memory on a computing device (or controller) in imaging system 200. In an embodiment, computing device 216 may include the instructions in non-transitory memory, and may apply the methods described herein, at least in part, to measure the AIF or TUC signals from a plurality of reconstructed images after receiving the reconstructed images from image reconstructor 230. The computing device 216 may then enter the AIF or TUC signal to a model to estimate the AIF and VOF curves, as described below, in order to optimally plan personalized contrast scan prescriptions, as described below. In other embodiments, image reconstructor 230 may include such executable instructions in non-transitory memory, and may apply the methods described herein to adaptively plan and control contrast scans. In yet another embodiment, the methods and processes described herein may be distributed across image reconstructor 230 and computing device 216.

In one embodiment, the display 232 allows the operator to evaluate the imaged anatomy, view measured and/or estimated AIF and VOF curves, trigger aspects of the contrast scans, and the like. The display 232 may also allow the operator to select a region of interest (ROI) and/or request patient information, for example, via a graphical user interface (GUI) for a subsequent scan or processing.

FIG. 3 shows a graph 300 depicting an example AIF curve 302, an example VOF curve 304, and an example tissue uptake curve (TUC) 306 each plotted as HU as a function of time. AIF curve 302 represents the change in the arterial inflow of a contrast agent over time for a patient, and VOF curve 304 represents the change in the venous outflow of the contrast agent over time for the patient. The AIF curve 302 may be measured at an arterial ROI, such as anterior cerebral artery or internal carotid artery, and may include a measurement of signal intensity in the arterial ROI relative to a baseline intensity (e.g., in the arterial ROI prior to contrast injection). The VOF curve 304 may be measured at a venous ROI, such as the superior sagittal sinus, and may include a measurement of the signal intensity in the venous ROI relative to a baseline intensity (e.g., in the venous ROI prior to contrast injection). TUC 306 may represent the change in detected contrast agent in a tissue of interest, as the contrast agent is taken up by the tissue and then depleted from the tissue. To measure the TUC, tissue of interest (e.g., the brain parenchyma) may be segmented in each of a plurality of reconstructed images, and the overall or average HU in the segmented region of each of the plurality of reconstructed images may be determined relative to a baseline level and plotted over time. Additional details regarding the tissue segmentation and TUC signal measurement are provided below with respect to FIG. 6.

The AIF curve 302 may include an arterial ascent knee at approximately point A on the curve, an arterial peak at point B on the curve, and an arterial decent knee at approximately point C on the curve. The amount of time from contrast injection until the arterial peak is reached may be the time to arterial peak, indicated as t_AP on FIG. 3. The VOF curve 304 may include a venous ascent knee at approximately point P on the curve, a venous peak at point Q on the curve, and a venous decent knee at approximately point R on the curve. The amount of time from contrast injection until the venous peak is reached may be the time to venous peak, indicated as t_VP on FIG. 3. The amount of time from contrast injection until the venous return to baseline (VRTB) is reached may be the time to VRTB, indicated as t_VRTB on FIG. 3. TUC 306 may include an ascent knee at approximately point U on the curve, a TUC peak at point V on the curve, and a decent knee at approximately point W on the curve.

The amount of time it may take to reach the points marked on the curves in FIG. 3 may vary from patient to patient, as body weight, cardiac function, and other factors may impact the contrast agent inflow and outflow rate. As will be explained in more detail below, certain contrast scan protocols, such as angiography scans, rely on the AIF and/or VOF curves, and the timing of one or more of the points described above (e.g., the arterial peak) may be determined and used as a trigger for adjusting scan parameters. However, some scan protocols are condensed as much as possible so that diagnostic information may learned as quickly as possible in order to facilitate patient care. For example, scan protocols carried out as part of an acute stroke assessment may be designed to be as short as possible, while still collecting the needed diagnostic image information, so that needed patient care may be administered as quickly as possible. Thus, the amount of time needed to completely measure the AIF curve, the VOF curve, and/or the TUC for a patient prior to initiation of the diagnostic scan(s) may delay patient care and negatively impact patient outcomes. Further, when the imaging system includes x-rays directed to the patient (such as the CT system described above with respect to FIGS. 1-2), it may be desired to minimize patient radiation exposure. Thus, acute stroke and other contrast scan protocols may include a short measurement of the AIF curve, for example, and scan protocol adjustments may be based on this limited information and/or certain aspects of the scan protocols may be carried out with fixed timing that is not changed from patient to patient. While such protocols may be suitable for ensuring that most scans generate sufficient diagnostic information, some scans may result in images that are not suitable for diagnosing the patient condition or may lead to unnecessary radiation exposure.

Thus, prior to or during a contrast scan, some or all of the TUC or the AIF curve may be measured and this TUC or AIF curve measurement (referred to as a TUC signal or an AIF signal) may be used to estimate the remainder of the TUC, the remainder of the AIF curve, and/or the VOF curve, as well as used to estimate various contrast curves (e.g., AIF and VOF) and/or time points of interest at different anatomical regions. For example, the TUC may measure contrast kinetics at the brain, and TUC may be used to estimate contrast kinetics at the aortic arch or other anatomical region. To ensure an accurate estimation, a machine learning model may be deployed that is trained using a plurality of different TUC and/or AIF signals measured from different patients as inputs along with ground truth data that may include associated full AIF, TUC, and/or VOF curves (or associated points of interest on the AIF, TUC, and VOF curves, such as the points labeled on FIG. 3 and described above) at various anatomical regions (e.g., the head and neck/aortic arch). The measured TUC signal or AIF signal may be entered into the trained and validated machine learning model, and the model may output an estimated AIF curve, estimated TUC, and estimated VOF curve, or the model may output the time to one or more significant points of the TUC and AIF and VOF curves, such as the time to arterial peak, the time to venous peak, and the time to venous return to baseline, for the head and/or the neck. The scan protocols may then be adapted on the fly on a patient by patient basis using the estimated TUC and AIF and VOF curves and/or estimated time points of the TUC and AIF and VOF curves.

FIG. 4 shows a graph 400 depicting an estimated AIF curve 402, an estimated VOF curve 404, and an estimated TUC 406, each estimated according to a TUC estimation method. The tissue uptake of a contrast agent (e.g., of a contrast bolus) may be monitored and used to set parameters for the in-flight contrast scan. As shown, a first segment 408 of the TUC is measured as described above (e.g., a change in HU level relative to a baseline level measured across a plurality of images). The first segment 408 may commence when the contrast bolus is administered (e.g., at time t1 in FIG. 4) and end after the TUC peak (e.g., at time t2 in FIG. 4). The first segment 408 may be entered into a model to estimate the remaining portion of the estimated TUC 406 and all of the estimated AIF curve 402 and VOF curve 404. As a result, time points U and V are measured while time points A', B', C', P', Q', and R' are estimated.

FIG. 5 shows a graph 500 depicting an estimated AIF curve 502, an estimated VOF curve 504, and an estimated TUC 506 each estimated according to an AIF estimation method. The inflow of the contrast agent of the contrast bolus may be monitored and used to set parameters for the contrast scan. As shown, a first segment 508 of the AIF curve is measured as described above (e.g., in a ROI based on change in HU level relative to a baseline level). The first segment 508 may commence when the contrast bolus is administered (e.g., at time t1 in FIG. 5) and end after the arterial peak (e.g., at time t2 in FIG. 5). The first segment 508 may be entered into a model to estimate the remaining portion of the estimated AIF curve 502, the TUC 506, and/or all of the estimated VOF curve 504. As a result, time points A and B are measured while time points P', V', C', Q', W', and R' are estimated.

Thus, the TUC and AIF and VOF curves (or selected time points of the TUC and AIF and VOF curves) may be estimated using a relatively short measured segment of the TUC or the AIF curve that is entered into a machine learning model. While the AIF estimation method was described as being based on a single arterial ROI, it is to be understood that multiple arterial ROIs could be measured and combined (e.g., averaged) to measure the AIF curve. Further, the VOF curve could be measured for the same time period as the AIF curve (e.g., from time t1 until the respective time t2) by monitoring a venous ROI, and the measured segment of the VOF curve could be used as input to the model in addition to the measured segment of the AIF curve, which may result in a more robust estimation of the remaining portions of the AIF and VOF curves.

The arterial ROI and venous ROI described above may be positioned at any suitable location where arterial inflow and venous outflow, respectively, of contrast agent may be detectable, and the selection of where to position the arterial ROI and/or venous ROI may depend on the scan protocol (e.g., what anatomy is going to be imaged in the contrast scan). However, some anatomy, such as the brain, may present challenges for arterial or venous ROI placement, as the ability to visualize certain anatomical features may require presence of a contrast agent. Thus, to place an arterial or venous ROI in the head/brain, a separate administration of contrast agent may be needed to even place the ROI, which may make arterial or venous ROI placement in the head unpractical. As such, the arterial ROI and/or venous ROI may typically be placed in the neck area or another adjacent anatomy, and then the patient may be moved relative to the CT imaging system (e.g., via table movement) to position the head in the proper location for the contrast scan. However, this additional table movement may prolong the duration of the scan session and/or make some adaptive scan protocols unpractical. Thus, some scan protocols may utilize the TUC estimation method in order to determine the various time points of interest/individual patient contrast kinetics. Accordingly, the AIF, TUC, and VOF curves (or selected time points of the AIF, TUC, and VOF curves) may be estimated using a relatively short measured segment of the TUC that is entered into a machine learning model.

A CT angiogram or angiography scan (referred to as a CTA scan) may produce diagnostic images showing blood vessels supplying blood to a tissue of interest, such as a brain, heart, etc. An example of a typical CTA scan prescription of the head and neck may include a CT acquisition or series of acquisitions, following injection of a contrast bolus, where the acquisitions begin at the neck and end at the head. Ideally, the CT acquisitions may be performed during contrast enhancement (e.g., during the arterial peak) at each anatomical location. In some examples, two or more additional CT acquisitions of the head may be performed, and these additional acquisitions may be timed based on patient contrast kinetics as well. Because different patients have different contrast kinetics, each CTA scan prescription may include a series of monitoring scans before the diagnostic acquisitions are performed in order to time the acquisitions to the patient's individual contrast kinetics. However, these monitoring scans are time consuming and may tie up processing resources, which may delay when the diagnostic images are reconstructed and available for aiding in clinical decisions.

Thus, according to embodiments disclosed herein, prior knowledge of a patient's contrast kinetics may be used to time CTA acquisitions for the patient during a CTA scan, when a contrast enhancement curve of the patient is available. The contrast enhancement curve may be generated during a prior contrast scan, if a contrast scan was performed on that patient within a threshold amount of time of starting the CTA scan (e.g., 15 minutes). Some scan protocols, such as those administered to assess acute stroke, may include a CT perfusion (CTP) scan followed in rapid succession by a CTA scan. When a CTP-CTA scan is performed, the patient's contrast kinetics may be monitored during the CTP scan by measuring the TUC signal of the head of the patient as described above. The TUC signal may be used to estimate one or more time points of interest at the neck/aortic arch of the patient, such as the arterial peak at the aortic arch. The CTA scan may be performed upon injection of a contrast bolus, with the first CTA acquisition starting at the base of the neck occurring at the estimated arterial peak at the aortic arch. Additionally, because the first CTA acquisition may be a head and neck acquisition terminating at the top of the head, and because the CTA acquisition at the head may preferably be performed at the arterial peak at the head, the CT system (e.g., the CT system table) may be controlled to automatically move the patient in concert with the contrast agent flow from the aortic arch to the head, so that the CTA acquisition at the head may be performed at the proper time. As used herein, the head and neck CTA acquisition (also referred to as the first CTA acquisition) may be understood to include multiple passes/acquisitions that may be performed successively as the patient is moved, such that at least one acquisition is taken at the base of the neck and at least one acquisition is taken at the top of the head. When the CT system is a helical CT system, the table may be moved while the gantry is rotated and acquisitions are taken continuously in a helical manner around the patient. When the CT system is an axial CT system, the neck acquisition may be performed, then the table may be moved to position the patient such that the head acquisition may be performed.

Figure 6A:
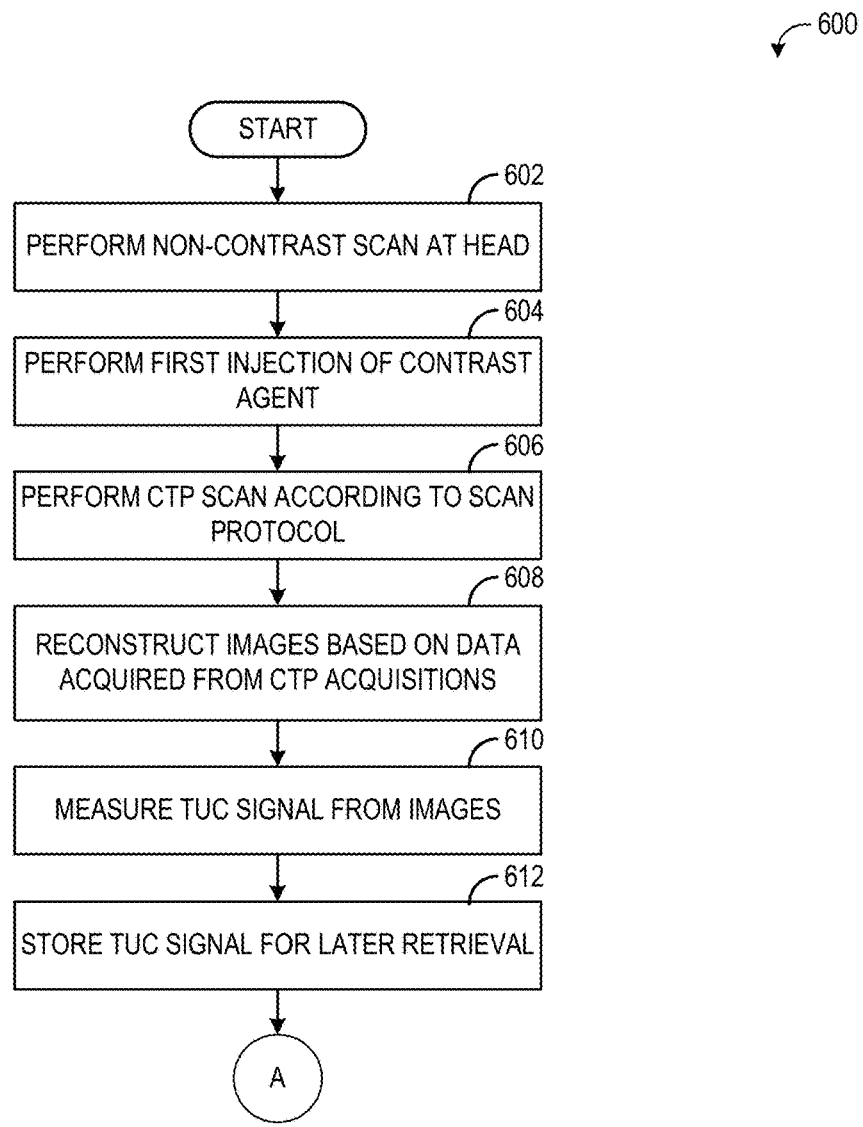
FIGS. 6A and 6B show a flow chart illustrating a method for performing an adaptive angiography scan, according to an embodiment of the disclosure.
Figure 6B:
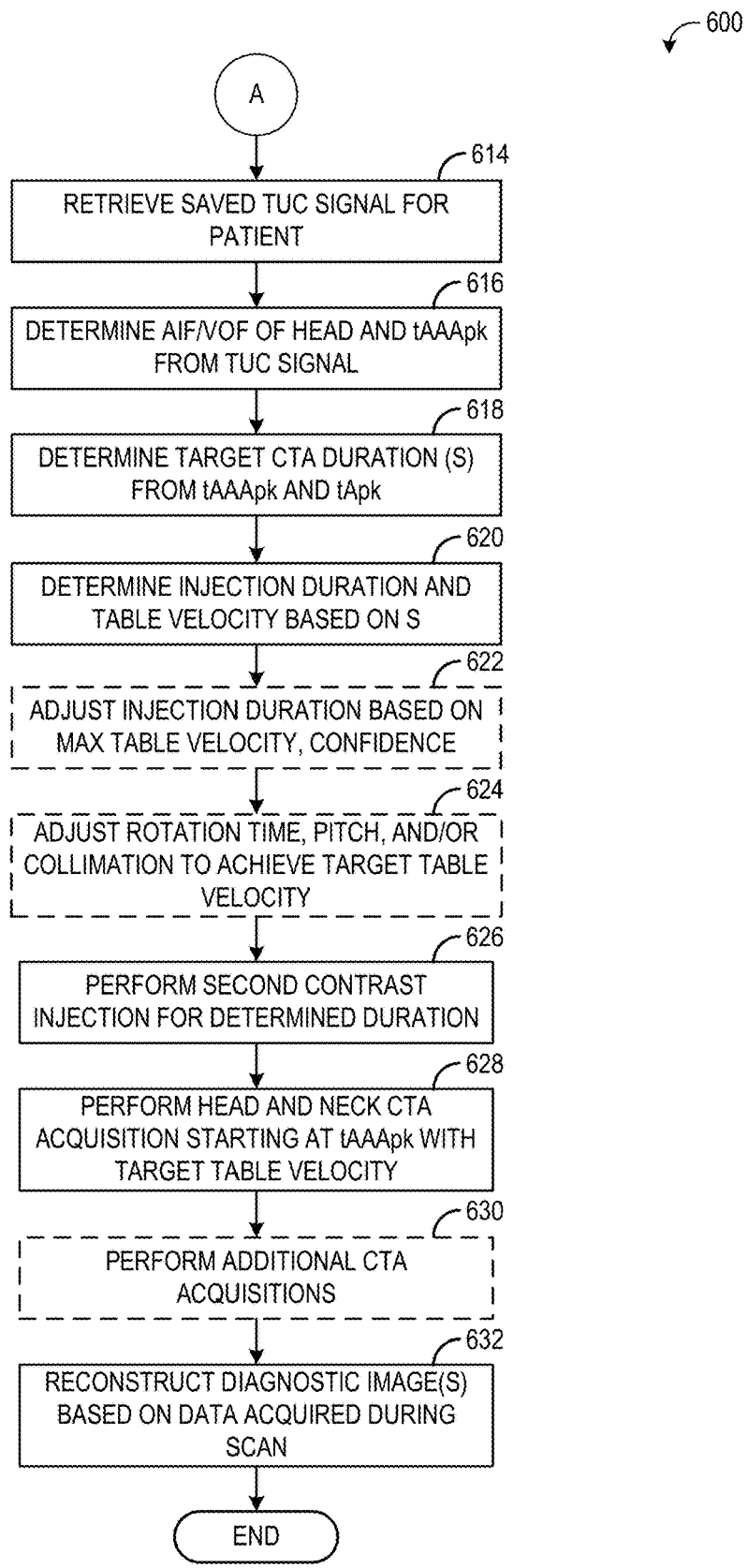

FIGS. 6A and 6B show a flow chart illustrating a method 600 for carrying out a personalized, adaptive CTA scan. Method 600 is described with respect to the system and components described above with respect to FIGS. 1-2 but could be carried out with other systems/components without departing from the scope of this disclosure. Method 600 may be carried out according to instructions stored in non-transitory memory of a computing device (e.g., computing device 216 of FIG. 2). Method 600 may include identification of estimated CTA acquisition timings based on prior knowledge of the patient's contrast kinetics. Thus, method 600 may be performed in response to user selection of a scan protocol that includes a CTA, such as a CTP followed by a CTA, though aspects of the method may be performed for any CTA where prior knowledge of the patient's contrast kinetics is available.

At 602, a non-contrast scan is optionally performed. The non-contrast scan may be taken to establish a baseline image for the area to be monitored before delivery of a contrast agent. The baseline image may then be used to align the patient and the region of interest within the imaging device. The non-contrast scan may be of the head in the example method presented herein, but it is to be understood that the non-contrast scan may be performed at another suitable anatomical region depending on the scan protocol. At 604, a first injection of contrast agent into the patient is performed. As a non-limiting example, the contrast agent may comprise iodine. As other examples, the contrast agent may comprise an ionic contrast medium such as meglucamine diatriozoate, or a non-ionic contrast medium such as iopromide or ohexol. The contrast agent may be intravenously injected using either automatic or manual methods. The injection may be a contrast bolus for an in-flight CTP scan and, in some examples, may be the only contrast injection performed for the CTP scan. At 606, a CTP scan may be performed according to a CTP scan protocol. The CTP scan protocol may include a CTP scan prescription that dictates the scanning resolution (e.g., temporal acquisition rate of the CTP passes), timing of the commencement and cessation of the acquisitions and/or transitions between different temporal acquisition rates, etc., as well as predefined x-ray source current(s) and predefined x-ray source voltage(s). The temporal acquisition rate may also be referred to as a temporal sampling rate and may include the frequency at which imaging system acquisitions (also referred to as passes) are performed. As used herein, a scan acquisition or pass may refer to a full gantry rotation (e.g., when the brain is being imaged) or a partial gantry rotation (e.g., when the heart is being imaged). In either case, an acquisition or pass may include the amount of gantry rotation that is needed to obtain the desired views for the anatomy/scanning protocol.

At 608, one or more images are reconstructed from the data acquired during the CTP acquisitions. In some examples, the images may be coarse images that may be reconstructed using a coarse reconstruction process that has a low computational load and thus may be performed rapidly. In such examples, the images reconstructed at 608 are not diagnostic images but instead are images reconstructed to monitor the tissue uptake of the contrast agent, and thus the coarse reconstruction process may sacrifice diagnostic quality in order to allow the images to be quickly reconstructed. The coarse reconstruction process may include 128×128 slices that are 5 mm thick, and the reconstruction process may take about 1 second per acquisition. In other examples, the images may be diagnostic images of full diagnostic quality reconstructed according to a scan prescription for the CTP scan.

At 610, the TUC signal is measured from the images. Measuring the TUC signal may include segmenting, in each image, a tissue of interest, such as the brain. The segmentation process may include thresholding the image, performing an erosion process on the thresholded image, identifying the largest object, and then performing a dilation process. However, other segmentation processes may be carried out without departing from the scope of this disclosure. Once the tissue of interest has been segmented, the overall or average signal intensity (e.g., pixel brightness) for the segmented region may be determined and compared to a baseline intensity (e.g., of that tissue/segmented region prior to contrast injection). The signal intensity of each segmented image may be determined and plotted as a function of time that the image was acquired to generate the TUC signal. However, in some examples, rather than relying on reconstructed images to measure the TUC signal, the TUC signal may be measured using the projection data acquired during the CTP acquisitions, without performing a full reconstruction process on the projection data. At 612, the TUC signal is stored (e.g., in memory of the computing device 216 or another suitable memory in communication with the computing device) for later retrieval.

Method 600 proceeds to 614 of FIG. 6B to retrieve the saved TUC signal for the patient. In the example presented in method 600, the TUC signal measured during the CTP scan performed immediately before the CTA scan is used to personalize/adapt the CTA scan (as explained in more detail below). However, in other examples, the TUC signal that is retrieved at 614 may be a TUC signal measured during a timing bolus, a CTP scan performed on the patient at an earlier point in time, or other suitable scan, so long as the TUC signal was measured within a threshold amount of time of execution of the CTA scan (e.g., 15 minutes or less), so that a likelihood that the patient's contrast kinetics will have changed is low. Further, in some examples, the TUC signal may be extracted from reconstructed CTP images rather than measured during the CTP acquisitions as described above.

At 616, the AIF and VOF curves of the head of the patient and the time to the arterial peak at the aortic arch (tAAApk) of the patient are determined from the TUC signal. For example, an AIF curve and a VOF curve at the head of the patient may be estimated from the TUC signal (and/or the time for the arterial peak (AP), venous peak (VP), venous return to baseline (VRTB), and/or other time points of interest may be estimated). Further, an AIF curve and hence the tAAApk (and other time points of interest, such as the time to the venous peak) at the aortic arch/base of the neck may also be estimated from the TUC signal.

The AIF and VOF curves and tAAApk may be estimated from the TUC signal by inputting the TUC signal into a machine learning model. As explained above, the TUC signal may include a measured segment of the TUC (which may include the entirety of the TUC in some examples) that may be used as input to a model, and the model may output the estimated AIF curves, the estimated VOF curve, and/or the tAAApk. The model may be a suitable machine learning model, such as a decision tree, regression model, neural network, and so forth. The regression model may include a bootstrap algorithm that is trained with a dataset of N samples, where each sample includes a measured signal (whether entire AIF and VOF curves and/or TUC, or select features such as the inflection points on each curve, rate of change of various segments of the curves, curve peak times and heights, and/or curve knee times and heights) from a respective patient and identified (e.g., by an expert) ground truth, such as HU and time values for certain points of interest on the AIV, VOF, and TUC curves of the head (e.g., A, B, C, Q, R, U, V, W), as well as time points of interest at the aortic arch, such as the arterial peak, venous peak, arterial washout, and venous washout, such that a plurality of measured signals and corresponding ground truths from a plurality of different patients are included in the dataset. The bootstrap algorithm creates random sub-samples of the dataset with replacement to output multiple values of a desired statistic, such as a mean. The average of those multiple values provides a robust estimate of the statistic. For example, the bootstrap algorithm may be applied to determine multiple values of each of a mean time to arterial peak, a mean time to venous peak, and a mean time to venous return to baseline, with each mean value correlated to an input measured signal. In some examples, the bootstrap algorithm may be aggregated where predictions (e.g., of the means described above) from multiple decision trees may be combined to reduce variance and overfitting. Cross-validation may be performed, where the input data (e.g., training dataset) is divided into n subsets, the regression model is trained with n−1 subsets, and the remaining subset is used to test the model to avoid overfitting.

In another example, the model may be a neural network that includes artificial neurons (referred to as units or nodes) arranged in a series of layers. The input units of the neural network receive information (e.g., the TUC signal), hidden units of the network process the information, the processed information is connected on positive or negative weights, and output units of the network signal a response to the learned information. In some examples, prior knowledge is used to reduce variance and improve generalizations and training data is run through the network and used to continuously change the weight vector of the network in response to a cost function, which improves the probability of an accurate output. In other words, the neural network may comprise a plurality of nodes/layers, including an input layer that receives the TUC signal and an output layer that outputs an estimated head AIF curve, an estimated head VOF curve, an estimated neck AIF curve and/or an estimated tAAApk (or estimated time to arterial peak, time to venous peak, time to venous return to baseline, and/or other time points), with connections/weights of the layers/nodes determined based on a training dataset. The training dataset may include a plurality of pairs of data, with each pair of data including measured contrast enhancement curves (e.g., AIF, VOF, TUC) and an associated TUC signal, or with each pair of data including a TUC signal and corresponding time points of interest for a plurality of patients (e.g., t_AP, t_VP, t_VRTB, tAAApk, etc.).

In some examples, monitoring scan data obtained prior to the CTP acquisitions may also be input to the machine learning model (e.g., in addition to the TUC signal). In order to time the CTP acquisitions appropriately for the patient, a series of low-dose monitoring passes may be performed at a monitoring ROI, which may be the neck of the patient in some examples, and thus the monitoring scan data may include a segment of an AIF curve at the neck of the patient. Thus, the entire TUC and the monitoring scan data may be input to the model, with an AIF inflection point ground truth at the base of neck used to train the model. The model may output the neck AIF curve as a function of the head TUC, the head AIF/VOF curves as a function of TUC, and the tAAApk as a function of the TUC.

In still further examples, a statistical/proxy method may be used to determine the tAAApk. For example, the tAAApk may be determined as a simple function of the head AIF, such as based on the equation tAAApk=tApk_head−D, where D is a function of the time to the arterial ascent knee of the head (tAknee_head) and the time to the arterial peak of the head (tApk_head), and thus D=f(tAknee_head, tApk_head), where the function may be linear, non-linear, or based on a look-up table. In general, the function may relate the time for the blood to flow from the aortic arch to the head to the time for the contrast to enhance from the arterial knee to the arterial peak, which may be determined from the head AIF. In one example, D=E*tAknee_head+F*tApk_head+a G, where E, F, and G are constants. As an example, E may be −0.5, F may be 1.5, and G may be −1.5. In some examples, additionally or alternatively, instead of defining tAAApk as a function of the head AIF, tAAApk may be defined as a function of the head TUC with appropriate substitutions. For example, the model may output the head AIF/VOF as a function of the TUC and a formula may be applied to estimate tAAApk as a function of the head AIF or the head TUC.

Thus, a model or statistical method may be applied to determine the tAAApk and other time points of interest, including the tApk (the time to the arterial peak at the head) from the TUC as measured during a prior scan, such as the CTP described above. As will be explained in more detail below, the head and neck CTA acquisition may be timed following administration of a contrast bolus to commence at the arterial peak of the neck/aortic arch, as determined from the tAAApk. The tAAApk and the tApk may be used to determine an amount of contrast agent to inject for the contrast bolus, in order to minimize the contrast load on the patient. The contrast load may be minimized when the CTA acquisition at the aortic arch/base of the neck is aligned as accurately as possible with peak enhancement of the aortic arch, and the load may also be minimized when the travel velocity of the table on which the patient is supported (e.g., table 114) is matched to the contrast-enhanced blood travel velocity. Accordingly, the tAAApk and the tApk may be used to determine an injection duration for the contrast bolus injection, as explained below, which will deliver a minimum contrast load to the patient.

At 618, a target CTA duration (S) is determined from the tAAApk and the tApk. The target CTA duration may be the amount of time demanded for performing the head and neck CTA acquisition, tracking the velocity of the contrast-enhanced blood flow from the aortic arch to the head. In some examples, the target CTA duration may be determined according to S=tApk_head−tAAApk+ψ, where ψ is an error term such that 0 s<|ψ|<1 s. Clinically, [tApk_head−tAAApk] is between 1-5 seconds and as such the limits of S may be 1 s<S<6 s.

At 620, an injection duration for the contrast bolus and a table velocity for the CTA scan are determined based on S. The table velocity may be determined based on S and a scan range of the patient. The scan range of the patient may be the distance between where the head and neck CTA acquisition will commence (e.g., the base of the neck) and where the head and neck CTA acquisition will terminate (e.g., the top of the head), and thus the scan range is the amount the table will be moved over the duration of the head and neck CTA acquisition. The scan range may be determined based on user input (e.g., a user may specify the scan range for the CTA prior to the CTP commencing or prior to the CTA commencing) or automatically using a camera or other sensors. The table velocity may then be determined by dividing the scan range by the CTA duration. As an example, if the target CTA duration is 3 s and the scan range is 35 cm, the target table velocity will be 11.66 cm/s. If the table can be adjusted to the target table velocity (such that the table can be moved to match the velocity of the contrast-enhanced blood flow), the injection duration may be set to a preset minimum injection duration, such as five seconds.

In some examples, method 600 may optionally include adjusting the injection duration based on a maximum table velocity and/or a confidence of the determination of S. If the table cannot keep up with S (e.g., the determined table velocity is higher than a maximum table velocity), then the injection duration may be extended proportional to the lag. For example, standard CTA length is ~35 cm. For a particular patient, S may be 2 s, resulting in a target table velocity of 17.5 cm/s. If the fastest that the CT system can perform the head and neck CTA acquisition is 3 s (e.g., with a maximum table velocity of 11 or 12 cm/s), the duration may be extended by the actual acquisition time−S. In the example presented above, the 5 s minimum injection duration may be extended by 1 s to be 6 s. It is to be appreciated that the maximum table velocity as described herein may not only be limited by the physical speed constraints of the table itself, but also may be limited by the acquisition parameters for the CTA, such as slice thickness, number of slices, and so forth. As will be explained below, the acquisition parameters may be adjusted to achieve the determined table velocity, but the amount the acquisition parameters may be adjusted may be limited in order to ensure images with necessary quality can be reconstructed.

Further, the injection duration may be adjusted based on the confidence of S, which is determined based on the confidence of estimating tAAApk and tApk from the TUC signal as explained above. For example, the model used to estimate tAAApk and tApk may output a relative confidence of the estimation of tAAApk and tApk, such as very high, high, medium, or low confidence. Additional time may be added to the injection duration based on the confidence, such as 1, 2, 3, or 5 s, respectively. Based on the above example, if tAAApk and tApk were estimated with medium confidence, then the injection duration may be extended by 3 s for a final duration of t1=6+3=9 s. In this way, the amount of contrast agent that is delivered in the contrast bolus prior to performing the CTA scan may be minimized while still ensuring sufficient contrast agent is present at the estimated arterial peak at the neck and the estimated arterial peak at the head.

At 624, one or more CTA acquisition parameters, such as gantry rotation time, pitch, and/or collimation may be adjusted (e.g., relative to rotation time, pitch, and/or collimation specified by the selected scan protocol) to achieve the target table velocity explained above. In some examples, gantry rotation time may be adjusted first, as adjustments in gantry rotation time may not negatively affect image quality. Then, upon adjusting the rotation time, if the table velocity is not reached, one or more of pitch and collimation may be adjusted, which may lower image quality. In other examples, only rotation time (or pitch or collimation) may be adjusted. In still further examples, different combinations of rotation time, pitch, and/or collimation may be preset, with each combination resulting in a different table velocity. The combination that results in a table velocity that is the closest to the target table velocity may be selected.

At 626, a second contrast injection is performed for the determined injection duration. The second contrast injection may be performed at a suitable time following the initial contrast scan (e.g., the CTP scan as described above with respect to FIG. 6A), such as once the contrast agent from the first contrast injection has washed out (e.g., at an estimated venous return to baseline of the first contrast injection). The second contrast injection may be performed manually or automatically and may include the same contrast agent as the first contrast injection. When the second contrast injection is performed manually, a prompt may be displayed (e.g., on display device 232) instructing the user to perform the contrast injection for the determined injection duration.

At 628, the head and neck CTA acquisition is performed, starting at the estimated tAAApk and with the table moved at the target table velocity, so that the head and neck CTA acquisition may finish at the top of the head at the estimated tApk. In this way, the CTA may commence using an automatically-determined prep delay between the contrast injection for the CTA and the first CTA acquisition, where the prep delay is set as the estimated tAAApk. Prior to performing the first CTA acquisition (e.g., the head and neck CTA acquisition), the table may be moved so that the base of the neck/aortic arch of the patient is positioned at an imaging position relative to the gantry/bore of the CT system (at the isocenter or other predefined position) when the first CTA acquisition is performed. Further, the table may be pre-accelerated so that the table is moving at the target table speed when the first CTA acquisition commences.

In some examples, the CTA may be a multi-phase CTA (mCTA) with one or more additional CTA passes performed after the head and neck CTA pass. In such examples, method 600 may include performing additional CTA passes at 630. The additional CTA passes may be performed at times based on the estimated VOF of the head, such as a second head CTA pass performed at the venous peak and a third head CTA pass performed at the venous return to baseline.

At 632, one or more diagnostic images are reconstructed based on data acquired during the CTA scan and, when performed, the CTP scan. For example, one or more diagnostic images may be reconstructed using known reconstruction techniques, such as filtered back projection or iterative reconstruction. The images may be reconstructed based on data acquired from each CTA and/or CTP acquisition. Further, the image reconstruction of the diagnostic images may be performed in parallel with the coarse reconstruction described above, at least in some examples. The one or more diagnostic images may be output to a display device (e.g., display device 232) for display to an operator or a physician, to a storage medium (e.g., mass storage 218) for retrieving at a later time, and so on. Method 600 may then end.

FIG. 7A shows a timeline 700 for a dual CTP-CTA scan, where the CTA scan is performed according to prior protocols where one or more monitoring scans are performed prior to the CTA. A CTP acquisition process 702 is performed first, where a plurality of CTP acquisitions are performed following a first contrast injection, starting at time t_CTPstart. After the CTP acquisitions are complete, a CTP image reconstruction process 704 is carried out whereby the data acquired during the CTP acquisition process 702 is reconstructed into one or more images. During the CTP image reconstruction process 704, the CTA acquisition process 708 may also be carried out, starting at t_CTAstart. The CTA acquisition process 708 may include a baseline scan (e.g., non-contrast scan), ROI placement, a second contrast injection, one or more monitoring scans that may be used to measure an initial part of an AIF curve of the patient, and the CTA acquisitions. During a portion of the CTA acquisition process 708, the CT system may be placed into high-demand mode to carry out and the monitoring scans for generating the AIF curve. The high-demand mode may tie up shared processing resources due to the real-time evaluation required for the monitoring scans. As such, the high-demand mode may disrupt the CTP image reconstruction that is occurring in parallel with the CTA acquisition process, thus prolonging the amount of time required for reconstructing the CTP images.

After the CTP image reconstruction process 704, a CTP post process 706 may be carried out where CT perfusion maps are generated. A CTA image reconstruction process 710 may be carried out in parallel, where images are reconstructed from the CTA acquisitions. The CTA image reconstruction process 710 may end before the CTP post process 706, at the time shown in timeline 700 as t_CTAstart+t_CTAduration-1. The CTP post process 706 may end at t_CTPstart+t_CTPduration-1.

FIG. 7B shows a timeline 750 for a dual CTP-CTA scan, where the CTA scan is performed according to the method of FIGS. 6A and 6B. A CTP acquisition process 752 is performed first, where a plurality of CTP acquisitions are performed following a first contrast injection, starting at time t_CTPstart. After the CTP acquisitions are complete, a CTP image reconstruction process 754 is carried out. During the CTP image reconstruction process 754, the CTA acquisition process 758 may also be carried out, starting at t_CTAstart. The CTA acquisition process 758 may include only the CTA acquisitions following the second contrast injection, and may not include a baseline scan (e.g., non-contrast scan), ROI placement, or one or more monitoring scans. Thus, the CT system may not be placed into the high-demand mode to carry out the monitoring scans. As a result, the disruption of the CTP image reconstruction that is occurring in parallel with the CTA acquisition process may be avoided or minimized, thus shortening the amount of time required for reconstructing the CTP images (e.g., by 1-3 minutes).

After the CTP image reconstruction process 754, a CTP post process 756 may be carried out where CT perfusion maps are generated. A CTA image reconstruction process 760 may be carried out in parallel. The CTA image reconstruction process 760 may end before the CTP post process 756, at the time shown in timeline 700 as t_CTAstart+t_CTAduration-2. The CTP post process 756 may end at t_CTPstart+t_CTPduration-2.

As appreciated by comparing FIGS. 7A and 7B, the overall duration of the CTA performed according to the methods disclosed herein (t_CTAduration-2) may be shorter than the overall duration for the CTA performed according to conventional methods (t_CTAduration-1), due to the elimination of the baseline scan, ROI placement, and monitoring scans (and associated table movements). Further, because the CTA according to the disclosed method eliminates the monitoring scans, the CTP image reconstruction process may also be shortened. Thus, the overall duration of the CTP performed according to the methods disclosed herein (t_CTPduration-2) may be shorter than the overall duration for the CTP performed according to conventional methods (t_CTPduration-1). As a result, both CTA images and CT perfusion maps may be available earlier when the CTP-CTA scans are carried out according to the methods disclosed herein, which may expedite patient diagnosis and improve patient care.

While the CTP-CTA scan described above may result in decreased scan times for a majority of patients, the CTA carried out according to the method of FIGS. 6A and 6B relies on an accurate estimation of the tAAApk and tApk, which may be challenging to estimate in some patients. For example, some patients may not exhibit a definable TUC peak. In such cases, the model or method applied to determine tAAApk and tApk, for example, may not be able to return an estimation of tAAApk and tApk, or the estimation may be of low confidence. If tAAApk and tApk cannot be estimated (or the estimation is too low in confidence to be trusted), the CTA acquisitions may not be performed, or the CTA acquisitions may be performed at the wrong time, which may delay output of clinically useful CTA images.

Thus, the CTA scan disclosed herein may be initialized with a fallback prescription that includes a conventional CTA sequence (e.g., baseline scan, ROI placement, contrast injection, monitoring scans, and the CTA acquisitions). If a TUC signal is available from a prior scan or timing bolus and relevant time points of interest can be estimated from the TUC signal (e.g., tAAApk and tApk) within a threshold amount of time, the CTA may instead be carried out according to an updated prescription that includes an updated injection duration and the head and neck CTA acquisition carried out at the estimated time points as described above with respect to FIGS. 6A and 6B. In this way, when possible, the CTA may be adapted and acquisitions moved forward in time, but if the prior knowledge of the patient's contrast kinetics is not available or informative, the standard CTA may still be carried out, thereby avoiding any rescans or unacceptable delays.

FIG. 8 is a flow chart illustrating a method 800 for adapting a fallback CTA prescription using prior knowledge of a patient's contrast kinetics. Method 800 is described with respect to the system and components described above with respect to FIGS. 1-2 but could be carried out with other systems/components without departing from the scope of this disclosure. Method 800 may be carried out according to instructions stored in non-transitory memory of a computing device (e.g., computing device 216 of FIG. 2). Method 800 may include identification of estimated CTA acquisition timings based on prior knowledge of the patient's contrast kinetics. Thus, method 800 may be performed in response to user selection of a scan protocol that includes a CTA, such as a CTP followed by a CTA, though aspects of the method may be performed for any CTA.

At 802, upon selection of a CTP-CTA scan protocol, a CTA is initialized with a fallback prescription and a CTA start time is determined at the start of a CTP scan. When the operator of the CT system is ready to perform a CTP-CTA scan on a patient, the operator may select a desired CTP-CTA scan protocol, where the CTP-CTA scan protocol includes a scan prescription for the CTP scan and a scan prescription for the CTA scan. As described above, each scan prescription may dictate when each scan is to start, the acquisition rate and timing for each scan, x-ray tube parameters for each scan, etc. The CTA scan prescription may include a fallback prescription that will be automatically implemented if the system cannot adapt the CTA scan prescription by the CTA start time. Because the CTA start time may be relatively close to the end of the CTP scan, the system may initialize (e.g., load and be ready to execute) the fallback CTA scan prescription at the start of the CTP scan, to avoid delaying the CTA scan or other issues in the event that the CTA scan prescription cannot be adapted, as explained below.

The CTA start time that is determined at 802 may be based on the shorter duration of the CTA scan (including image reconstruction) relative to the CTP scan and the lack of clinical value in having the CTA images ready more than a minute or two earlier than the CT perfusion maps. The CTA start time may be determined by calculating a best case CTP duration that includes the durations for the CTP acquisitions, image reconstruction, and perfusion map generation, such as the t_CTPduration−1 illustrated in FIG. 7A, and a worst case CTA duration that includes the baseline scan, ROI placement, monitoring scans, CTA acquisitions, and image reconstruction, such as the t_CTAduration−1 of FIG. 7A. In one example, tCTAstart=t_CTPstart+t_CTPdurtion−t_CTAduration, with the constraint that tCTAstart>=min_tCTA_start=t_CTPstart+t_CTP_Acquisition+minimum wait time determined by population statistics of the site where the CT system is located. As an example, for a certain site, min_tCTA_start=120 s. In other words, the CTA start time may be timed to occur after the CTP acquisitions end (following a minimum wait time).

At 804, the CTP scan is performed according to the CTP scan prescription. Performing the CTP scan may include performing a first contrast injection and then performing a plurality of CTP acquisitions over a duration. The CTP scan may be adaptive, in which case the number of acquisitions and/or duration over which the acquisitions are performed may be adjusted based on an AIF or TUC signal that is measured at the start of the CTP scan and/or as the CTP scan progresses. In other examples, the CTP scan may be fixed with a fixed number and/or timing of acquisitions.

At 806, a plurality of images are reconstructed based on data acquired from the CTP acquisitions and at 808, a TUC signal is measured from the images. The image reconstruction and TUC signal measurement may be performed in the same manner as the image reconstruction and TUC signal measurement performed at 608 and 610, respectively, of FIG. 6A, and thus description of the image reconstruction of 608 and the TUC signal measurement of 610 of FIG. 6A likewise applies to the image reconstruction of 806 and the TUC signal measurement of 808.

At 810, the TUC signal is analyzed to determine one or more CTA parameters for adapting the CTA scan prescription, which will be explained in more detail below with respect to FIG. 9. Briefly, the TUC signal may be analyzed to determine if the TUC signal is sufficient to estimate tAAApk and tApk, for example. The analysis may include determining if enough data has been collected (e.g., at least a threshold number of data points have been added to the TUC signal for the model or statistical method to estimate tAAApk and tApk) and if the TUC signal is reasonable enough (e.g., includes a definable peak) that a medium to high confidence of tAAApk and tApk can be determined. If the TUC signal is reasonable, tAAApk and tApk may be estimated, along with a target table velocity and injection duration for the CTA contrast injection.

At 812, method 800 determines if the CTA parameters have been determined before the CTA start time. If the CTA parameters (e.g., tAAApk and tApk, the table velocity, and/or the injection duration) have been determined prior to the CTA start time (e.g., that was defined at 802), method 800 proceeds to 814 to perform the CTA according to the updated CTA scan prescription at a CTA start time, which in some examples may also be updated (e.g., relative to the start time defined at 802). Performing the CTA according to the updated scan prescription may include performing a contrast injection with updated injection parameters, as indicated at 816. For example, as explained above with respect to FIG. 6B, the contrast injection duration may be shortened relative to the contrast injection duration for the fallback scan prescription, since the monitoring scans are eliminated. Performing the CTA according to the updated scan prescription may also include initiating the head and neck CTA acquisition at the estimated tAAApk (following the contrast injection) and finishing the head and neck CTA acquisition at the estimated tApk (following the contrast injection), as indicated at 818. The neck and head CTA acquisition starting and ending at tAAApk and tApk, respectively, may be performed as described above with respect to FIG. 6B, including moving the table supporting the patient at the determined table velocity. Further, in some examples, because the updated CTA scan prescription eliminates the baseline scan, ROI placement, and monitoring scans, the duration of the CTA scan may be shortened. As a result, in some examples, the CTA start time may be updated relative to the CTA start time defined at 802. In some examples, the CTA start time may be delayed, so that the CTA images are available at the same time as the images would be available in the fallback scan prescription. In other examples, the CTA start time may be advanced relative to the CTA start time defined at 802, if the patient has relative rapid contrast enhancement and hence the patient's CTP acquisitions are performed faster than expected (e.g., the CTA start time may be at or before the patient's venous return to baseline or another adaptive timing). The CTA may be considered to be "started" when the second contrast injection commences, and thus the CTA start time (whether updated or not) may be the time that the second contrast injection commences.

At 820, one or more diagnostic images are reconstructed based on data acquired during the CTA scan. For example, one or more diagnostic images may be reconstructed using known reconstruction techniques, such as filtered back projection or iterative reconstruction. The images may be reconstructed based on data acquired from each CTA acquisition. Further, images may be reconstructed based on data acquired during the CTP scan, and one or more perfusion maps may also be generated based on the data acquired during the CTP scan. The one or more diagnostic images may be output to a display device (e.g., display device 232) for display to an operator or a physician, to a storage medium (e.g., mass storage 218) for retrieving at a later time, and so on. Method 800 may then end.

Returning to 812, if the CTA parameters are not determined before the CTA start time (e.g., if tAAApk and tApk cannot be estimated, or if they are estimated at a low confidence), method 800 proceeds to 822 to perform the CTA according to the fallback prescription at the CTA start time. Performing the CTA according to the fallback prescription may include placing the CT machine in a high-demand mode and taking a baseline scan (e.g., non-contrast scan) to position a ROI for subsequent contrast enhancement monitoring, as indicated at 824. Performing the CTA according to the fallback prescription may also include performing a contrast injection with default parameters, as indicated at 826. The default injection parameters may include a given concentration of contrast agent (e.g., 350 mg/ml) delivered a given rate (e.g., 4 ml/sec) for a default duration (e.g., 17.5 sec). On the other hand, when the injection parameters are updated as performed at 816, the contrast agent may be injected at the same concentration and rate, but may be injected for a shorter duration (e.g., 4-5 sec).

Performing the CTA according to the fallback prescription may also include monitoring an AIF curve generated from data collected during monitoring scans at the ROI, as indicated at 828. The AIF curve generated and monitored at 828 may be similar to the AIF curve illustrated in FIG. 5, though a shorter segment may be monitored (e.g., monitoring may be terminated after the arterial ascent knee). Performing the CTA according to the fallback prescription may also include placing the machine in a diagnostic/low-demand mode after monitoring of the AIF curve is complete, moving the table, and initiating the head and neck CTA acquisition based on the monitored AIF curve, as indicated at 830. Once the generating/monitoring of the AIF curve is complete, the first CTA pass (and the subsequent CTA pass(es)) may be performed at a time determined from the monitored AIF curve. In some examples, the table may be moved prior to performing the first CTA pass (e.g., to position the aortic arch/base on the neck for imaging and so that the table is moving at a target velocity when the first CTA pass is performed). Further, the CT system may be adjusted so that x-ray dosage is higher relative to the high-demand mode used for the monitoring of the AIF (e.g., for obtaining data suitable for reconstructing diagnostic images) and/or other scan parameters may be adjusted (e.g., rotation time, pitch, slice thickness, etc.). Method 800 proceeds to 820 to reconstruct the diagnostic images, as explained above, and then method 800 ends.

FIG. 9 is a flow chart illustrating a method 900 for determining CTA parameters based on a TUC signal. Method 900 may be performed as part of method 800, in order to determine the CTA parameters for updating the CTA scan prescription. At 902, method 900 performs a next CTP acquisition. At 904, one or more images are reconstructed based on data acquired from the CTP acquisitions. As explained above with respect to FIG. 6A, the images may be reconstructed in an interleaved manner with the CTP acquisitions, which may result in at least one image being reconstructed for each CTP acquisition. As more CTP acquisitions are performed, more images are reconstructed. However, in other examples, the images may be reconstructed in another suitable manner, or the TUC signal may be measured using the projection data without full image reconstruction, as explained above with respect to FIG. 6A. At 906, the TUC signal generated from the images is analyzed. For example, the average HU may be determined for each coarse image and plotted as a function of time. Thus, as more CTP acquisitions are performed and hence more coarse images are reconstructed, the TUC signal may periodically grow/update.

As the TUC signal is generated, the TUC signal may be analyzed to determine if the TUC signal is sufficient and/or suitable for determining the CTA parameters. The analysis may include inputting the TUC signal into the model and/or applying the statistical method described above with respect to FIG. 6B. If the model and/or statistical method is able to generate the AIF curve, VOF curve, and/or the tAAApk, as explained above with respect to FIG. 6B, the TUC signal may be indicated as sufficient. In some examples, if the AIF curve, VOF curve, and/or the tAAApk are determined with low confidence, the TUC signal may be indicated as insufficient. If the model and/or statistical method is not able to generate the AIF curve, VOF curve, and/or the tAAApk, the TUC signal may be indicated as being insufficient.

In another example, the analysis of the TUC signal may include determining if a peak in the TUC signal has been detected, and if the detected peak is a plausible peak. For example, a peak detector may be executed that is configured to directly detect a peak in the TUC signal and evaluate whether the detected peak is the TUC peak (e.g., time point V on FIG. 3) by determining if the detected peak meets one or more rules that define the TUC peak. The peak detector may, for each CTP acquisition, look for a peak that has a double confirm (e.g., the peak may be double confirmed when two successive CTP acquisitions are performed, each having a lower measured HU than the detected peak). If a confirmed peak is found, the found peak is considered as an internal peak candidate (IPC). If the IPC occurs before a threshold time since the contrast injection (e.g., 14 seconds), the IPC may be discarded and the process may be repeated on the next IPC. If the IPC does not occur before the first threshold time, the IPC is further analyzed to determine if the slope of the IPC is greater than a threshold slope, such as 3 HU/s. If so, that IPC is considered a spike and is discarded. If not, the time between the ascent knee (e.g., time point U on FIG. 3) and the IPC is determined. If this time is less than a second threshold time, such as 4 seconds, the IPC is considered a spike and discarded. If not, it is determined if the median HU before the IPC is greater than a threshold value, such as the IPC HU minus 2. If so, the IPC is discarded. If not, the segmented tissue (e.g., brain) volume of the image acquisition at the IPC is compared to the segmented tissue volume from the previous image acquisition. If the segmented tissue volume at the IPC is different from the previous tissue volume by an amount that is greater than a threshold (e.g., 4.25%), the IPC is discarded. If not, (and if none of these described conditions are triggered), the IPC is confirmed as the tissue peak. If a plausible TUC peak is detected in the TUC signal, the TUC signal may be indicated as being sufficient. If a plausible TUC peak is not detected in the TUC signal, the TUC signal may be indicated as being insufficient.

If the TUC signal is determined to insufficient, method 900 proceeds to 922 to determine if the current elapsed time since the CTP start time (e.g., the time since the contrast injection for the CTP or the time since the first CTP acquisition) is within range of the CTA time. In some examples, being in range of the CTA start time may include being equal to the CTA start time. In some examples, being in range of the CTA start time may include being within a threshold amount of time of the CTA start time, such as within 1-5 seconds of the CTA start time. Because the TUC signal is updated with each CTP acquisition, the TUC signal may be deemed insufficient simply due to an insufficient number of CTP acquisitions having been performed and thus too small of a TUC segment/signal available to analyze. As such, if the CTA start time has not yet been reached (e.g., NO at 922), method 900 may loop back to 902 to perform the next CTP acquisition and continue to generate and analyze the TUC signal.

If the current time since the CTP start is within the range of the CTA start, method 900 proceeds to 924 to continue to execute the fallback CTA scan prescription (e.g., proceeding to 822 of FIG. 8), and then method 900 ends. Once the CTA start time is reached (or just prior to the CTA start time being reached), the window for being able to adapt to the CTA scan prescription closes, as the CTA start time represents the time at which the CTA has to be started in order to complete the CTA scan according to the fallback CTA scan prescription before the CTP scan is complete.

Returning to 908, if the TUC signal is determined to be sufficient to be able to determine the CTA parameters for updating the CTA scan prescription, method 900 proceeds to 910 determine the AIF/VOF curves of the head and the tAAApk from the TUC signal, as explained above at 616 of FIG. 6B. At 912, the target CTA duration (S) is determined from tAAApk and tApk (where tApk is determined from the AIF curve), as explained above at 618 of FIG. 6B. Further, at 914, the injection duration and the target table velocity are determined based on S (and the scan range), as explained above at 620 of FIG. 6B. At 916, method 900 optionally includes adjusting the injection duration based on the maximum table velocity and confidence, as explained above at 622 of FIG. 6B. At 918, method 900 optionally includes adjusting one or more of the rotation time, pitch, and/or collimation of the CT system to achieve the target table velocity, similar to the adjustment(s) performed at 624 of FIG. 6B. At 920, the CTA scan prescription is updated with the determined CTA parameters. For example, the fallback scan prescription that was initialized at the start of the CTP scan may be updated and/or replaced with an adaptive scan prescription that adjusts the CTA parameters as described herein, including the injection duration of the second contrast injection, the target table velocity for moving the table during the CTA scan (which may include adjustments to the rotation time, pitch, and/or collimation), and the timing (e.g., relative to the start of the second contrast injection) of the initiation of the head and neck CTA acquisition. Method 900 then ends.

Thus, the methods described above with respect to FIGS. 8 and 9 provide for a execution of a fallback CTA scan prescription that may be adapted on the fly based on individual patient contrast agent kinetics, in order to eliminate the pre-CTA monitoring scans and reduce the duration (and hence total amount) of contrast agent injected for the CTA. In doing so, the duration of the CTP scan may also be reduced, due to more shared processing resources being available to reconstruct the CTP images during the CTA scan. The adaptation of the fallback scan prescription may be performed only if certain CTA parameters may be determined within a predetermined time frame. The fallback scan prescription may be a "worst case" CTA prescription with a baseline scan, ROI placement, and monitoring scans performed, along with a maximum amount of contrast agent. By initializing the CTA scan with the fallback prescription and then adapting if possible, rather than starting with a scan prescription that eliminates the monitoring scans and then either adapting or switching to the fallback if the CTA parameters cannot be identified, a more robust CTA scan may be performed for all patients.

In some examples, when the acquisitions are complete and as projection data is sent for image reconstruction/post-processing, the actual AIF/VOF curves (or TUC) may be generated as a first step to the perfusion map computation. In some examples, a post-scan workflow may include displaying to the user a comparison of the AIF/VOF/TUC estimates used to generate the CTP scan prescription vs the actual measured TUC and/or AIF and VOF curves. The differences between the estimated and measured AIF/VOF/TUC may be used to inform the user of the accuracy of the AIF/VOF estimates, inform the user of any errors in the estimates that might have impacted diagnostic image quality, and/or update the machine learning estimation models.

Further, while methods were described above with respect to a head and neck CTA scan using a TUC signal to adapt the CTA scan prescription, the methods may apply to other types of scans without departing from the scope of this disclosure. For example, the methods may be used to adapt CTA scans of the heart, lungs, kidneys, legs, arms, etc. Additionally, particularly when scanning other anatomical regions, an AIF signal may be monitored/used as the input to the ML model, rather than the TUC signal. In such examples, the AIF signal may be monitored for an AIF peak, in a manner similar to the peak detector described above. If a plausible AIF peak is detected, the AIF signal may be entered as input to the ML model to determine the CTA parameters (e.g., time to arterial peak for one or more anatomical locations), for example, and then the CTA scan prescription may be adapted as described above. If no AIF peak is detected, the fallback scan prescription may be executed.

Thus, as discussed herein, a personalized adaptive CTA scan may be carried out based on the patient-specific contrast signal and output of the machine learning and/or statistical model described above (e.g., based on estimated AIF and VOF curves of the head and estimated AIF, VOF, and TUC curves of the neck/aortic arch (or various time points of interest of the AIF, TUC, and/or VOF curves) each estimated from a TUC of the head). The CTA scan prescription may be defined by a head and neck CTA acquisition that commences at the base of the neck and terminates at the top of the head, and when the head and neck CTA acquisition is to start and the rate at which the patient may be moved during the head and neck CTA acquisition may be estimated using the machine learning model with the measured contrast signal (e.g., measured TUC signal) as input to the machine learning model. The scan prescription for the CTA scan (e.g., the CT system parameters for carrying out the scan) may be dynamically adapted during execution of the CTA scan based on the timing of the arterial peak at the head and the arterial peak at the base of the neck/aortic arch, such that the CTA scan may be carried out in a manner that is optimized for the specific patient without requiring pre-CTA scan monitoring scans. In doing so, total scan time may be reduced, radiation exposure may be lowered, and image quality may be maintained.

However, some patients may have TUCs (or AIF curves, depending on the contrast signal used to adapt the scan prescription) that may have a slow ascent, undetectable peak, or other parameter that may make estimating the various time points discussed herein (e.g., the arterial peaks at the head and at the neck) in a timely manner challenging. For example, when the TUC signal is entered as input to the ML model, the ML model may utilize the time that the TUC peak occurred as one aspect of the TUC signal that predicts the other time points/curves, such as the arterial peaks of the head and the neck. If a TUC peak is not detectable, the adaptation to the scan prescription may not function as intended. Thus, as described herein, a fallback scan prescription may be initially executed that is configured to sufficiently scan nearly all patients, where the fallback scan prescription may include the monitoring scans to time the start of the head and neck CTA acquisition. Prior to execution of the fallback scan prescription, the TUC signal may be generated and monitored for the TUC peak. If a TUC peak is detected, the TUC signal may be entered as input to the ML model to estimate the other time points/curves, and the scan prescription may be adapted on the fly based on the estimated other time points/curves. If a TUC peak is not detected within a predetermined time frame, the fallback scan prescription may be executed to complete the CTA scan. In this way, sufficient scanning may be ensured regardless of when, or if, a TUC peak is detected.

FIG. 10 shows a set of plots 1000 showing parameters of an example CTP-CTA scan carried out for a first patient. A first plot 1002 shows a TUC signal (in HU) measured during the CTP scan of the first patient. A second plot 1010 shows scanning events (with the tube current (mA) for each acquisition period) over time for the first patent for the CTP scan. A third plot 1020 shows contrast injection events for the CTP-CTA scan (in mL). A fourth plot 1030 shows scanning events (with the tube current mA) for the CTA scan of the patient.

As shown by the set of plots 1000, a first CTP acquisition may commence after a prep delay following start of a first contrast injection 1022 at time t1. The acquisitions of the CTP scan may be carried out at a suitable acquisition rate and tube current as dictated by the CTP scan prescription. A TUC 1004 is measured from the coarse images reconstructed from data from the CTP acquisitions. The TUC is used to adapt the CTA scan prescription. For example, as explained above, the TUC (and any pre-CTP monitoring scan data) may be entered into a machine learning model that may be trained to output estimated AIF and VOF curves for the head based on the TUC, as well as estimated AIF and/or VOF curves for the aortic arch and/or the time to the arterial peak of the aortic arch (tAAApk). The first plot 1002 includes an estimated AIF curve 1006 for the head that may be output based on the TUC 1004.

The estimated AIF curve 1006 may be analyzed to determine the time to the arterial ascent knee for the head (tAknee_head), which occurs at time t2 in the set of plots 1000, and the time to the arterial peak for the head (tApk), which occurs at time t3. The tAknee_head is shown by arrow 1009 and the tApk is shown by arrow 1011. Further, the machine learning model may output the tAAApk, which is shown by arrow 1013. In some examples, the machine learning model may output the estimated AIF curve, and the tAAApk may be determined based on the estimated AIF curve, such as according to the equation tAAApk=tApk−D, where D=E*tAknee_head+F*tApk+G and E, F, and G are constants. In this way, the tAAApk may be determined to occur some amount of time before the tApk, where the amount of time is based on the velocity of the contrast-enhanced blood flow for the patient.

Because a sufficient TUC 1004 was measured that allowed for the estimated AIF curve 1006 to be generated, the CTA scan prescription is adapted to eliminate the baseline scan, ROI placement, and monitoring scans. Thus, at a commanded time (shown as time t4), the second contrast injection 1024 commences. The second contrast injection 1024 may be minimized as explained above, and thus may have a duration of 4-6 s, for example, ending at time t5. At the tAAApk following the initiation of the second contrast injection 1024, the head and neck CTA acquisition commences (e.g., at time t6), ending at the tApk (shown at time t7).

Next, FIG. 11 shows a set of plots 1100 showing parameters of an example CTP-CTA scan carried out for a second patient. A first plot 1102 shows a TUC signal (in HU) measured during the CTP scan of the first patient. A second plot 1110 shows scanning events (with the tube current (mA) for each acquisition period) over time for the first patent for the CTP scan. A third plot 1120 shows contrast injection events for the CTP-CTA scan (in mL). A fourth plot 1130 shows scanning events (with the tube current mA) for the CTA scan of the patient.

As shown by the set of plots 1100, a first CTP acquisition may commence after a prep delay following start of a first contrast injection 1122 at time t1. The acquisitions of the CTP scan may be carried out at a suitable acquisition rate and tube current as dictated by the CTP scan prescription. A TUC 1104 is measured from the coarse images reconstructed from data from the CTP acquisitions. However, unlike TUC 1004, TUC 1104 does not include a definable TUC peak. Rather, TUC 1104 includes two spikes occurring earlier than would be expected for a TUC peak, followed by a steady contrast level. As such, TUC 1104 cannot reliably be used to estimate the head AIF and VOF curves, and cannot reliably be used to estimate tAAApk.

Thus, once the CTP scan has completed and at a determined CTA start time (t2), the CTA scan may be carried out according to the fallback scan prescription. At time t2, a second contrast injection 1124 commences, with the second contrast injection 1124 ending at time t3. A series of monitoring acquisitions 1132 are then performed (e.g., at a lower mA), which may be plotted in real time to generate an AIF segment 1106. The timing of the head and neck CTA acquisition 1134 may be determined based on the AIF segment 1106. As shown, the head and neck CTA acquisition commences at time t4.

As appreciated by the set of plots 1000 and the set of plots 1100, when the fallback scan prescription is performed, the duration of the contrast injection for the CTA may be longer than when the CTA scan prescription is adapted (e.g., the second contrast injection 1124 may be performed for 17.5 s, relative to the 4-6 s for the second contrast injection 1024). Further, the CTA scan may have a longer duration when the fallback scan prescription is followed relative to the adapted scan prescription. For example, the head and neck CTA acquisition shown in plot 1030 may commence at time t6 of FIG. 10. The plots shown in FIGS. 10 and 11 are all time-aligned, and thus time t6 of FIG. 10 corresponds to just before time t3 of FIG. 11. The head and neck CTA acquisition 1134 of plot 1130 commences at time t4. Further, the adapted scan prescription shown by FIG. 10 does not include the pre-CTA monitoring scans, in contrast to the monitoring acquisitions 1132 of FIG. 11 performed as part of the fallback prescription.

FIG. 12 is a flow chart illustrating a method 1200 for defining an adaptive contrast scan protocol. Method 1200 is described with respect to the system and components described above with respect to FIGS. 1-2 but could be carried out with other systems/components without departing from the scope of this disclosure. Method 1200 may be carried out according to instructions stored in non-transitory memory of a computing device (e.g., computing device 216 of FIG. 2). Method 1200 may include the selection/adjustment of various parameters for one or more contrast scan protocols. Thus, method 1200 may be performed in response to authenticating an authorized personnel, such as a lead technologist, radiologist, hospital administrator, etc.

At 1202, a user input specifying an adaptive scan protocol to modify is received. In some examples, the computing device may store a plurality of default contrast scan protocols, and the user input may include a selection of one of the default contrast scan protocols. In other examples, the computing device may store one or more modified contrast scan protocols, and the user input may include a selection of one of the modified contrast scan protocols. In still further examples, the user input may include an indication that a new contrast scan protocol is to be defined. The contrast scan protocol may be a suitable contrast scan protocol, such as a CTP followed by a CTA, or a CTA following a timing bolus, or (at least initially) a stand-alone CTA. The contrast scan protocol may be specific to a particular anatomy and/or a particular suspected patient condition. For example, the contrast scan protocol may be specific to a head, head/neck, abdomen, heart, etc., and/or the contrast scan protocol may be specific to acute stroke, myocardial infarction, liver dysfunction, etc. Further, additionally or alternatively, the contrast scan protocol may be specific to a type of patient, such as pediatric, adult, advanced age adult, small, medium, large, etc. The user input may be received from a suitable user input device, such as the operator console 220 (which may include a keyboard, a mouse, a touchscreen, and/or another suitable input device).

At 1204, an adaptive scan protocol graphical user interface (GUI) is displayed. The adaptive scan protocol GUI may be displayed on a display device communicatively coupled to the computing device, such as display 232. The adaptive scan protocol GUI may include one or more sections via which various parameters for the contrast scan protocol may be set/adjusted, including a section to set an adaptive delay for initiating a CTA scan as will be explained in more detail below. An example of the adaptive scan protocol GUI is shown in FIG. 13.

At 1206, two contrast scans (e.g., a CTP and a CTA) may be linked based on user input to the adaptive GUI. For example, the selected scan protocol may include two contrast scans (e.g., a CTP followed by a CTA) and selection of the scan protocol may indicate that the user wants to link the two contrast scans. In other examples, the user may indicate, via the adaptive GUI, that two contrast scans are to be linked, and may indicate which types of contrast scans are to be linked (e.g., CTP and CTA) and in which order (e.g., CTP followed by the CTA). By linking the two contrast scans in the scan protocol, the two contrast scans may be performed in rapid succession when the scan protocol is executed, without a user having to separately select and execute individual scan protocols for each contrast scan at the time of scanning a patient. The user may also set aspects of the scan prescription for the first contrast scan via the adaptive GUI (e.g., the concentration, rate, and duration of a first contrast injection for the first contrast scan).

At 1208, the timing of a second contrast injection for the second contrast scan is set based on user input to the adaptive GUI. For example, the user may specify whether the second contrast injection is be performed at a timing determined on-the-fly for each individual patient (e.g., while the scan protocol is being implemented to scan the patient), or whether the second contrast injection is to be performed at a fixed timing. If the user specifies that the second contrast injection is to be performed at a fixed timing, the user may specify the fixed amount of time (e.g., 180s) that will elapse following a specified event (e.g., the end of the first contrast injection), at which the second contrast injection will commence. If the user specifies that the second contrast injection is to be performed at a time optimized for the individual patient, the user may specify one or more events and/or delays for the optimized injection timing (e.g., the user may specify that the second contrast injection is to occur 2 seconds after the venous return to baseline of the first contrast injection).

At 1210, method 1200 may determine if the user has indicated that the scan protocol include an adaptive CTA. For example, the adaptive scan protocol GUI may include an input (e.g., a toggle button or other user interface control element) that, when selected or activated, indicates that the CTA of the scan protocol is to be an adaptive CTA. If the user enters a user input indicating that the CTA is to be an adaptive CTA, method 1200 proceeds to 1212 to set a fallback CTA scan prescription with a fixed prep delay and injection duration. The fallback CTA scan prescription may be similar or the same as the fallback scan prescription described above with respect to FIG. 8, and thus may include a baseline scan, ROI placement, monitoring scans, and the CTA acquisitions. In some examples, the user may specify elements of the fallback scan prescription via the adaptive scan protocol GUI, such as the contrast volume of contrast agent to be delivered via the second contrast injection.

At 1214, an adaptive CTA scan prescription with a personalized prep delay is set. As explained above with respect to FIGS. 8 and 9, the adaptive CTA scan prescription may be carried out if prior knowledge of the patient's contrast kinetics is available (e.g., from the CTP preceding the CTA), where the adaptive CTA scan prescription may include adaptations to the contrast injection for the CTA, timing of the CTA acquisitions, and table velocity. Thus, setting the adaptive CTA scan prescription may include setting an adaptive injection duration based on user input to the adaptive scan protocol GUI, as indicted at 1216. For example, the adaptive scan protocol GUI may include one or more inputs via which the user may indicate if the injection duration (and hence volume) should be adapted or if the injection volume should be a fixed volume (e.g., matching the contrast volume of the injection for the CTP or another fixed volume). Further, setting the adaptive CTA scan prescription may include setting one or more adaptive table speed parameters based on user input to the adaptive scan protocol GUI, as indicated at 1218. As explained above, the table of the imaging system may be moved (when performing the head and neck CTA acquisition) at a target speed to match the contrast flow velocity. To achieve the target speed, one or more parameters of the CTA may be adjusted, such as the gantry rotation time, the pitch, and/or the collimation. The adaptive scan protocol GUI may include one or more inputs via which the user may enter user input to specify which parameter(s) may be adjusted to control table speed. In some examples, the user may select only one parameter that is to be adjusted to control table speed. In other examples, the user may select two or more parameters that may be adjusted to control table speed. In such examples, the user may specify a priority/order for adjusting the parameters and/or place limits around how much each parameter may be adjusted, in order to ensure that desired image quality is achieved.

At 1220, the information that is displayed via the adaptive scan protocol GUI may be updated based on the user input described above. For example, the adaptive scan protocol GUI may include a preview section that displays a visual representation of the scan protocol, where one or more generic/base contrast agent curves (e.g., an AIF curve, a VOF curve, and/or a TUC) are displayed and a visual representation of the automatically-determined prep delay may be displayed as part of the curves. Additional details of the adaptive scan protocol GUI, including adjustments to the preview section, are discussed below with respect to FIG. 13.

At 1222, the adaptive scan protocol is saved when indicated (e.g., in response to a user input commanding the protocol be saved). The saved protocol may be stored in mass storage 218 (with respect to FIG. 2) or within additional memory with in computing device 216 or on a network-accessible memory (e.g., the cloud, a PACS system, etc.). The saving of the scan protocol may include saving any adjustments made to the scan protocol. The scan protocol may then be retrieved at a later time and executed in order to scan a patient according to the parameters specified in the scan protocol, as explained below with respect to FIG. 14. Method 1200 may then end.

FIG. 13 shows an example adaptive scan protocol GUI 1300 that may be displayed on a display device (e.g., display 232) in response to a user request to modify an existing adaptive scan protocol or in response to a user request to establish anew adaptive scan protocol. Adaptive scan protocol GUI 1300 is a non-limiting example of the adaptive scan protocol GUI that is displayed as part of method 1200 of FIG. 12. The adaptive scan protocol GUI 1300 shown in FIG. 13 is specific to a head perfusion and angiography scan protocol (e.g., a CTP-CTA scan), but it is to be understood that a similar adaptive scan protocol GUI may be displayed in order to set parameters for other types of contrast scans.

GUI 1300 includes a scan series section 1301 that includes a plurality of user interface control inputs via which the user may define the contrast scan(s) to be performed according to the scan protocol. In the example shown in FIG. 13, the scan series section 1301 facilitates user definition of a first scan series (e.g., a first contrast scan) and a second scan series (e.g., a second contrast scan). Thus, as shown, the scan series section 1301 includes a first scan series input 1302, a first injection concentration input 1304, a first injection volume input 1306, and a first injection rate input 1308. The first scan series input 1302 may present the user with a list of scan series names (e.g., via a dropdown menu), with each name identifying a scan series having a predefined scan prescription (e.g., a scan prescription stored in memory and/or being available to be linked or imported into the scan protocol currently being defined). For example, in FIG. 13, the user has selected a CTP for the first scan series. Via the first injection concentration input 1304, the first injection volume input 1306, and the first injection rate input 1308, the user may define values for each of the contrast agent concentration, volume, and injection rate for the first contrast injection of the first scan series.

The scan series section 1301 further includes a second scan series input 1310, a second injection concentration input 1312, a second injection volume input 1314, and a second injection rate input 1316. The second scan series input 1310 may present the user with the list of scan series names (e.g., via a dropdown menu), similar to the list presented via the first scan series input 1302. In FIG. 13, the user has selected a CTA for the second scan series. Via the second injection concentration input 1312, the second injection volume input 1314, and the second injection rate input 1316, the user may define values for each of the contrast agent concentration, volume, and injection rate for the second contrast injection of the second scan series. The second injection volume input 1314 may be configured to receive user input specifying a range of contrast volumes, rather than a fixed contrast volume. The range thus sets a lower limit and an upper limit on the injection volume, and the actual delivered injection volume may be determined at the time of the scanning the patient, as described for the adaptive CTA scan prescription. Once the user has selected the desired scan series, the scan prescription for each scan series may be loaded/stored as part of the scan protocol.

The scan series section 1301 also includes an adaptive timing input 1318. When selected, activated, or otherwise turned on, the adaptive timing input 1318 may cause the timing of the second contrast injection to be determined based on the individual patient's contrast kinetics. In response to the user selecting/activating the adaptive timing input 1318, additional views of the GUI 1300 may be displayed, via which the user may set parameters of how the start time of the second contrast injection is to be optimized/personalized. In the example shown, the user has not selected or activated the adaptive timing input 1318. Thus, a first fixed timing input 1320 and a second fixed timing input 1322 are displayed and made active (such that the inputs may receive user input). Via the first fixed timing input 1320, the user may specify a fixed amount of time (e.g., 180 seconds) after an event specified via the second fixed timing input 1322 (e.g., the end of the first contrast injection) at which the second contrast injection will commence.

The san series section 1301 also includes an adaptive CTA input 1319. Activation or selection of the adaptive CTA input 1319 causes the scan protocol to include an adaptive CTA scan prescription adapted for each individual patient based on the contrast curve(s) of the patient as determined during the CTP scan, as described above with respect to FIGS. 6A, 6B, 8, and 9. In response to the user selecting/activating the adaptive timing input 1319, additional sections of the GUI 1300 may become activated/available for accepting user input (e.g., a preview section 1330 and/or a CTA prescription section 1340), via which the user may set the contrast volume for the fallback prescription and the adaptive prescription, as well as set CTA parameters to adapt to reach a target table velocity, as described below. When the adaptive timing input 1319 is not selected/activated, the additional sections may be deactivated/unable to accept user input, at least partially. In such examples, the additional sections may change in visual appearance (e.g., go gray).

The preview section 1330 includes a set of generic contrast curves 1332. The generic contrast curves may include a generic (e.g., non-patient specific) AIF curve, TUC, and VOF curve and may be based on average AIF, TUC, and VOF curves for a plurality of patients, at least in some examples. The set of contrast curves 1332 may represent average contrast curves expected to be exhibited by a patient following a second contrast injection and may include a visual indication 1334 of when (on the set of contrast curves) the head and neck CTA acquisition is to occur following commencement of the second contrast injection (also referred to herein as an auto adaptive prep delay). Further, the preview section 1330 may include a visual indication of the prep delay 1336. The visual indication of the prep delay may be set to "TBD" or other indicator since the prep delay is determined for each patient at the time of scanning.

The CTA prescription section 1340 may include a fallback subsection 1342 and an adaptive subsection 1344. In the fallback section 1342 and the adaptive subsection 1344, the parameters for the fallback and the adaptive CTA scan prescriptions are displayed, including an indication of whether or not monitoring scans will be performed (referred to herein as Smart Prep), an indication of whether the prep delay is fixed or adaptive, and an input where contrast volume may be defined. Thus, the fallback subsection 1342 includes an indication that Smart Prep will be enabled (e.g., that monitoring scans will be performed), that the prep delay is fixed and not adaptive, and a first contrast volume input 1346. The user may enter input to the first contrast volume input 1346 indicating the contrast volume that will be injected if the fallback CTA scan prescription is executed. The adaptive subsection 1344 includes an indication that Smart Prep will not be enabled (e.g., that monitoring scans will not be performed, as the contrast curve(s) measured during the CTP will act as the monitoring scans), an indication that the prep delay will be adaptive, and a second contrast volume input 1348 and a third contrast volume input 1350. The second contrast volume input 1348 may allow the user to indicate whether the contrast volume for the second contrast injection should match the contrast volume of the CTP. If the user selects or activates the second contrast volume input 1348, the volume of the second contrast injection will be automatically adjusted to match the volume of the first contrast injection, and the user may not be able to enter input in the third contrast volume input 1350. If the user does not select or activate the second contrast volume input 1348, the volume of the second contrast injection may be specified via the third contrast volume input 1350.

The CTA prescription section 1340 also includes an adaptive table speed input 1352. If the user selects or activates the adaptive table speed input 1352, the scan protocol will be set to adjust the table speed during the head and neck CTA acquisition to match the contrast travel time between the start and end locations of the head and neck CTA acquisition, as explained above with respect to FIGS. 6B, 8 and 9. If the user does not select or activate the adaptive table speed input 1352, the table speed during the head and neck CTA acquisition may be moved at a default speed that is not based on the individual patient's contrast flow.

If the user selects or activates the adaptive table speed input 1352, the user may specify which parameter is to be adjusted to adjust the table speed via a parameter input 1354. As shown, the parameter input 1354 is a drop-down menu that includes a list of selectable parameters, such as rotation time (as shown), collimation, and pitch. The parameter input 1354 may allow the user to select one parameter to be adjusted in order to match the table speed to the contrast flow, but other inputs are possible, such as allowing the user to select more than one parameter and/or rank the parameters in order of adjustment. Additional examples of how the GUI 1300 may be configured to allow the table speed to match the contrast flow are shown in FIGS. 16 and 17.

While not shown in FIG. 13, the adaptive scan protocol GUI 1300 may include a save input that, when selected, causes the specified scan protocol to be saved in memory, so that the specified scan protocol may be executed to scan a patient when desired, as will be explained in more detail below.

FIG. 14 shows a flow chart illustrating a method 1400 for performing a contrast scan according to an adaptive contrast scan protocol. Method 1400 is described with respect to the system and components described above with respect to FIGS. 1-2 but could be carried out with other systems/components without departing from the scope of this disclosure. Method 1400 may be carried out according to instructions stored in non-transitory memory of a computing device (e.g., computing device 216 of FIG. 2). Method 1400 may include the execution of a scan protocol in order to image a patient, where the scan protocol may be an adaptive scan protocol defined/adjusted according to the method of FIG. 12. Thus, method 1400 may be performed in response to authenticating an authorized operator, such as a lead technologist, a technologist, etc.

At 1402, a user input specifying an adaptive scan protocol to execute is received. In some examples, the computing device may store a plurality of adaptive scan protocols, and the user input may include a selection of one of the adaptive scan protocols. The adaptive scan protocol may be a suitable contrast scan protocol that includes two contrast scans, such as a CTP followed by a CTA. The selected scan protocol may be specific to a particular anatomy, a particular suspected patient condition, and/or a type of patient. The user input may be received from a suitable user input device, such as the operator console 220 (which may include a keyboard, a mouse, a touchscreen, and/or another suitable input device). In some examples, the selected scan protocol may be a scan protocol that is set/defined/adjusted according to method 1200 described above. Further, in some examples, the operator may enter a user input indicating that the scan protocol is to be executed (e.g., as opposed to modified). In other examples, the scan protocol may be executed automatically in response to the user selecting the scan protocol.

At 1404, the operator may be prompted to perform a scout scan of an imaging subject via a run-time graphical user interface (GUI). The scout scan may include a low-resolution scan that generates 2-dimensional images of the imaging subject from which the scan range/field of view of the following diagnostic scan may be set. In some examples, a notification prompting the user to perform the scout scan may be displayed as part of a run-time GUI, and the scout scan may be performed in response to a user input commanding the scout scan be executed. The run-time GUI may be displayed on a suitable display device associated with the imaging system, such as display 232. The run-time GUI may present scan information to the operator of the imaging system, such as patient information, scan parameter settings, dose information, etc., as will be explained in more detail below. In other examples, the user may command the imaging system to perform the scout scan without the imaging system prompting the user to perform the scout scan, or the scout scan may be performed automatically. In still further examples, no scout scan may be performed.

At 1406, a diagnostic scan range may be set via the run-time GUI. For example, the image(s) generated from the scout scan may be displayed via the run-time GUI along with one or more scan range overlays. The user may adjust the extent of the scan range overlays to set the diagnostic scan range. At 1408, some or all of the adaptive scan protocol GUI may be displayed within or along with the run-time GUI. Via the adaptive scan protocol GUI, the operator may view the set scan parameters for the selected scan protocol. In some examples, the operator may adjust the set scan parameters for the current scan via the adaptive scan protocol GUI, in the same manner as discussed above with respect to FIG. 12. However, if the operator adjusts any of the scan parameters, the adjustments may not be saved. In this way, one-time adjustments to the scan protocol may be made by the operator of the imaging system during a current scan, but the selected scan protocol may not be adjusted for subsequent scans.

At 1410, a CTP scan is performed upon a first contrast injection (e.g., in response to commencement or termination of the first contrast injection). Performing the CTP scan may include performing one or more acquisitions according to a scan prescription that is generated according to the selected scan protocol. The one or more acquisitions may be commenced once a contrast agent has been injected (and after a prep delay following the contrast agent injection). As a non-limiting example, the contrast agent may comprise iodine. As other examples, the contrast agent may comprise an ionic contrast medium such as meglucamine diatriozoate, or a non-ionic contrast medium such as iopromide or ohexol. The contrast agent may be intravenously injected using either automatic or manual methods. In some examples, such as when the contrast agent is injected manually (e.g., by the operator or another clinician), the operator may enter a user input indicating the contrast agent has been injected (which may notify the imaging system of when to begin acquisitions). Further, while not included in FIG. 14, some scan protocols may include a non-contrast scan of the intended/target anatomy, which may be performed before the injection of the contrast agent.

The scan prescription may include the number and timing of each acquisition, the system settings for each acquisition (e.g., x-ray source current and voltage), the scan range (e.g., scan stop and start locations) for each acquisition, table position for each acquisition, etc. The scan prescription may be determined from the scan parameters defined in the selected scan protocol and/or the scan prescription may be adjusted based on patient data. For example, various zones and/or phases of the scan protocol may start or end based on patient specific events, such as the peak of the patient's VOF curve or once the contrast agent has washed out of the patient. The patient data may inform on when these events will occur relative to the start of the contrast scan. The patient data may be determined from the initial acquisitions of the first contrast scan. For example, the contrast level of a specified anatomical feature (e.g., an artery) may be measured during the initial acquisitions of the contrast scan and plotted as a function of time. After a predetermined amount of time, or once a peak of a curve formed by the plotted contrast levels (or other suitable event) is detected, the measured segment of the curve may be used to predict when subsequent events are going to occur (e.g., venous peak and venous return to baseline), and the scan prescription may be updated on the fly based on the predicted time of these events. In some examples, these initial acquisitions may be of a different anatomical feature than the anatomy intended to be imaged in the diagnostic scan, and thus once the curve segment has been measured, the table supporting the imaging subject may be automatically moved to center the intended anatomy in the imaging system.

Additionally, during execution of the CTP scan, a contrast curve of the patient, such as a tissue uptake curve (TUC), may be generated, as explained above with respect to FIGS. 6A, 6B, 8, and 9. The contrast curve may be used to determine when the second contrast injection is to be performed (e.g., when the scan protocol dictates that adaptive injection be performed) and/or the contrast curve may be used to determine adaptive parameters of the CTA that will be performed after the CTP acquisitions are complete (e.g., the timing of the head and neck CTA acquisition, target table velocity, and injection volume).

At 1412, a notification of the scan progress and determined CTA parameters may be displayed via the run-time GUI. For example, the run-time GUI may include a visual indicator of the scan progress that may change as the scan progresses. The visual indicator may include one or more progress bars, which may indicate scan progression by progressively changing in color or brightness over time (e.g., from left to right across the progress bar), and may include relative timing of each acquisition and time between each acquisition for the first contrast scan (and the second contrast scan once the second contrast scan is performed, as explained below). Further, as the CTP scan progresses and the patient contrast curve (e.g., the TUC) is generated, various parameters of the CTA scan may be calculated, such as the adaptive prep delay (e.g., the time between commencement of the second contrast injection and the commencement of the head and neck acquisition). When the CTA parameters are calculated, one or more of the CTA parameters may be displayed via the run-time GUI. The CTA parameters may be displayed via the run-time GUI while the CTP acquisitions are still being performed (provided a sufficient patient contrast curve has been obtained) and/or once the CTP acquisitions are complete.

At 1414, at an injection timing determined according to the scan protocol, the user is prompted to perform a second contrast agent injection, or the second contrast agent is performed automatically. Additionally, the second contrast agent injection is performed for a duration determined according to the scan protocol. The injection duration may be determined as explained above with respect to FIGS. 6B, 9, and/or 13. For example, the scan protocol may include fixed injection volume as specified via the adaptive scan protocol GUI, as explained above with respect to FIG. 13, and thus the injection duration may be set based on the fixed volume. In other examples, the scan protocol may include an adaptive volume and hence duration that is determined based on the target table velocity, maximum table velocity, and/or confidence of determining the tAAApk and tApk, as explained above with respect to FIG. 6B.

Further, as explained above with respect to FIG. 8, the CTA may be initialized with a fallback scan prescription that may include a fixed, maximum injection volume, and thus the determination of the injection duration may be based on whether the fallback scan prescription is performed (e.g., due to not being able to determine the CTA parameters from the patient's contrast curve before the CTA start time) or the adaptive CTA scan prescription is performed. If the patient's individual contrast kinetics may be measured (e.g., via the TUC as described above and/or based on the contrast curve segment and machine learning model-based contrast curve performed as part of the first contrast scan) before the CTA start time is reached, the adaptive CTA scan prescription may be performed. In systems where an auto/power injector is not included, the user may be prompted (e.g., via a notification displayed as part of the run-time GUI) to perform the second contrast injection at the timing and duration indicated by the scan protocol.

At 1416, the CTA scan is performed. Performing the CTA scan may include performing one or more acquisitions according to a CTA scan prescription that is generated according to the selected scan protocol. As explained above, the CTA scan prescription may be the fallback CTA prescription or the adaptive CTA prescription. The one or more acquisitions may be commenced once the second contrast injection has been performed (or started) (and after a prep delay following the contrast agent injection). The scan prescription may include the number and timing of each acquisition, the system settings for each acquisition (e.g., x-ray source current and voltage), the scan range (e.g., scan stop and start locations) for each acquisition, table position for each acquisition, etc. The scan prescription may be determined from the scan parameters defined in the selected scan protocol and/or the scan prescription may be adjusted based on patient data, such as based on the contrast kinetics of the patient learned during the first contrast scan. For example, if the second contrast scan is a CTA, the acquisitions of the scan protocol may start or end based on patient specific events, such as the peak of the patient's AIF. The patient data may inform on when these events will occur relative to the start of the second contrast scan. Additionally, the progress of the second contrast scan may be provided via the run-time GUI, as explained above.

In some examples, the timing of the second contrast injection and/or updated scan prescription for the first contrast scan and/or second contrast scan may be displayed via the run-time GUI. For example, after a scan prescription is adjusted or once the timing of the second contrast injection is determined, a visual representation of the scan prescription and/or timing of the second contrast injection may be displayed as part of the run-time GUI, with the visual representation showing the patient's contrast level curve (as measured during the first contrast scan), a predicted patient contrast level curve occurring after the first contrast level curve, and a delay between the two curves based on the adaptive or fallback injection timing (once determined), similar to the preview section of the adaptive scan protocol GUI of FIG. 13. At 1418, a notification may displayed via the run-time GUI once the scan is complete. Additional details about the run-time GUI are provided below with respect to FIG. 15.

At 1420, one or more reconstructed images are displayed and/or stored. For example, one or more diagnostic images may be reconstructed from the data acquired during the contrast scan using known reconstruction techniques, such as filtered back projection or iterative reconstruction. The one or more diagnostic images may be output to a display device (e.g., display device 232) for display to an operator or a physician, to a storage medium (e.g., mass storage 218) for retrieving at a later time, and so on. Method 1400 may then end.

While method 1400 is described above as being implemented on the same computing device as method 1200 described above, in some examples method 1200 may be implemented on a separate computing device, such as an edge device, a cloud computing system, a server, etc. In such examples, the adaptive scan protocol GUI may be displayed, during execution of method 1200, on a display device associated with the separate computing device. When method 1400 is executed, the selected adaptive scan protocol may be sent from the separate computing device to the computing device executing method 1400. Such a configuration may allow a lead technologist to set adaptive scan protocol settings on one separate computing device, and those protocols may be sent out to multiple, separate imaging systems in communication with the separate computing device.

FIG. 15 shows an example run-time GUI 1500 that may be displayed on a display device (e.g., display 232) in response to a user request to execute an existing adaptive scan protocol. Run-time GUI 1500 is a non-limiting example of the run-time GUI that is displayed as part of method 1400 of FIG. 14.

The run-time GUI 1500 includes a scan prescription section 1510 where information about the scan prescription for each scan of the scan protocol for the imaging subject (e.g., patient) is displayed. The scan prescription may be generated based on the selected adaptive scan protocol and, in some examples, contrast level curve information for the patient. The run-time GUI 1500 also includes a progress bar 1520 that displays the current status/progress of the contrast scan. Additionally, the run-time GUI 1500 may include a patient information section 1530, a scan information section 1540, a scan range selection section 1550, and a dose information section 1560. In the patient information section 1530, information about the imaging subject may be displayed, such as a patient name and/or ID number, patient gender, and patient position (e.g., head first/supine). In the scan information section 1540, information about the scan protocol may be displayed, such as the name of the scan protocol and the sequences/series of the scan protocol (e.g., the scout scan, the non-contrast scan, and contrast scan or scans, which as shown in FIG. 15 includes a CTP followed by a CTA). Additionally, when a sequence of the scan protocol is completed, a checkmark or other visual indicator may be displayed. The current sequence may be highlighted or otherwise visually indicated. In the scan range selection section 1550, scout images of the imaging subject may be displayed with the current scan range displayed as an overlay on the scout image(s). The scan range may be adjusted by resizing the overlay(s). In the dose information section 1560, information about the x-ray radiation dose administered to the imaging subject may be displayed, such as projected dose, total accumulated dose, etc., so that the operator of the imaging system may monitor the patient's x-ray radiation exposure.

Run-time GUI 1500 may include a series of views as the contrast scans are completed. In the view shown in FIG. 15, a user (e.g., a technologist executing the scans on the patient) is viewing CTA scan settings/scan prescriptions before the CTA scan has commenced. In the scan prescription section 1510, the prescription for the CTA is shown, including the scan range for the CTA, the kV and mA for the CTA, contrast agent injection parameters for the CTA, the scan type (e.g., axial versus helical), reconstruction parameters, etc. While not shown in FIG. 15, the user may view scan settings/prescription for the CTP (e.g., by selecting the CTP from the scan information section 1540).

Further, run-time GUI 1500 may display a replicate of the adaptive scan protocol GUI 1512 (e.g., as shown in FIG. 13) so that the operator is given the opportunity to confirm the settings for the current adaptive scan protocol, and if desired, change any of the settings. Additionally, when sufficient data relating to the patient's contrast curve(s) has been obtained (e.g., during or following the CTP scan), the CTA scan prescription may be adjusted to include the adaptive CTA scan parameters discussed above, such as the adaptive prep delay/commencement of the head and neck CTA acquisition (e.g., tAAApk). As shown in FIG. 15, the replicate of the adaptive scan protocol GUI 1512 may be updated to show that the auto adaptive prep delay has been determined (herein, shown as being 27 s). Thus, the run-time GUI 1500 may visually indicate to the operator when the first CTA pass is set to commence, as determined based on the individual patient's contrast curve(s). Further still, the run-time GUI 1500 may include visual representations of additional adaptive scan parameters calculated based on the patient's contrast curve(s), such as the total scan time for the CTA (e.g., 60 s, shown above the progress bar 1520) and parameters of the coverage speed (e.g., the collimation, the pitch, the table velocity, the rotation time, etc.). For example, as shown, the collimation may be 40 mm, the pitch may be 516:1, the table speed may be 41.25 mm/s, and the rotation time may be 0.28 s. Further, the CTA scan duration (S) for the head and neck acquisition may be 6.0 s. As explained above, the CTA scan duration may be determined based on the patient's contrast curve and the scan range of the patient, which in the present example may be approximately 25 cm. Thus, the table speed may be set at 41.25 mm/s (e.g., to travel 25 cm in 6 s). The rotation time, collimation, and/or pitch may be selected (e.g., adjusted relative to the rotation time, collimation, and/or pitch set via the scan prescription) to allow the table to move at the set table speed, as explained above.

However, if sufficient data relating to the patient's contrast curve(s) cannot be obtained during the CTP scan (at least before the CTA start time), the run-time GUI 1500 may have a different visual appearance than shown in FIG. 15, e.g., the replicate of the adaptive scan protocol GUI 1512 may be adjusted to include or be replaced with a visual indication prompting the user to perform the monitoring scan. Because the fallback scan prescription for the CTA will be performed rather than the adaptive scan prescription, the parameters of the coverage speed (e.g., rotation time, pitch, collimation) may be the same as indicated in the original scan prescription.

Further, the run-time GUI 1500 may include one or more user interface inputs that, when selected by the operator, confirm the scan protocol setting and/or trigger the start of the contrast scan. When the user selects or otherwise enters input indicating to confirm the settings and/or start the scan, both the first and second contrast scans (e.g., the CTP and the CTA) may commence without further user input, at least in some examples.

As each contrast scan progresses, the progress bar 1520 may change in visual appearance. For example, the progress bar 1520 may include a waveform, with each raised segment of the waveform representing an acquisition. As the scan progresses, the color of the waveform may progressively change, e.g., turning gray to blue from left to right, in sync with the scan progress.

Thus, an adaptive contrast scan may be performed when a technologist selects a patient/unknown patient and an adaptive contrast scan protocol is selected (e.g., an adaptive contrast scan protocol as described herein). Upon selection of the adaptive contrast scan protocol, a scout scan is performed to acquire the scout images (e.g., shown in the scan range selection section 1550) and a non-contrast scan is performed (e.g., for determining the patient baseline). The scan protocol may include a 1-button confirm procedure, in which case the adaptive acquisition linked CTP/CTA series is launched (e.g., including the adaptive scan protocol GUI as described herein). The technologist may review the settings indicated via the adaptive scan protocol GUI at scan time, but may not have to adjust any settings defined by the lead technologist (e.g., as described above with respect to FIGS. 12 and 13). Once the technologist confirms the scan parameters (e.g., via selecting the "confirm settings" input shown in FIG. 15), the imaging system begins the CTP scan acquisitions. After the CTP concludes, the imaging system will show the remaining time to start the CTA via a delay indicator in the scan progress bar (e.g., the 27 s shown under the progress bar 1520 of FIG. 15), though other notification methods are possible, such as a traffic light, or a larger visual countdown on the GUI/display device. At this time, the run-time GUI may be updated to include the adaptive scan parameters as discussed above (e.g., the adaptive prep delay, the coverage speed parameters). At the end of the countdown, the adaptive CTA scan may commence. If a power injector is being used, then the system may automatically start the CTA scan and the contrast injection simultaneously. If a power injector is not being used, the system may activate the scan start button (e.g., put the button in a responsive state) and prompt the user to press the scan start button while simultaneously starting the injector.

If the protocol does not include a 1-button confirm procedure, the CTP is acquired first, then the run-time GUI may be updated to include the adaptive scan parameters as discussed herein. The user may then confirm the scan parameters (e.g., via the confirm settings input) and proceed to commence the CTA scan.

While the adaptive scan protocol GUI as shown in FIG. 13 included a simplified option for setting the scan parameters to be adjusted to reach the target table speed (e.g., a drop-down menu where a single parameter could be selected), in some examples, more than parameter may be adapted to reach the target table speed. FIGS. 16 and 17 show portions of example adaptive scan protocol GUIs including different inputs for setting multiple parameters for reaching a target table speed.

FIG. 16 shows a first example portion 1600 of an adaptive scan protocol GUI. Portion 1600 includes the adaptive table speed input 1352. If a user selects or activates the adaptive table speed input 1352, additional inputs for setting the parameters for adjusting the table speed to reach the target table speed may be activated. As shown in FIG. 16, these additional inputs may include a first input 1602, a second input 1604, and a third input 1606. Each input may include an ordering input, such as ordering input 1608, via which the user may specify the order in which to adjust each parameter. Each input may further include a parameter input, such as parameter input 1610, via which the user may specify the parameter that is to be adjusted (e.g., each parameter input may be a dropdown menu that includes a plurality of parameters, such as rotation time, collimation, pitch, and/or no parameter). For example, via ordering input 1608 and parameter input 1610, the user may specify that rotation time is to be adjusted first; via the other ordering inputs and parameter inputs, the user may specify that collimation is to be adjusted second and pitch is to be adjusted third. Alternatively, the user may specify collimation is be adjusted first or pitch is to be adjusted first, or set another suitable order of parameters, which may include only selecting one or two parameters to be adjusted in some examples. Further, in some examples, the ordering may be fixed and only the parameters may be selected, or the parameters may be fixed and only the ordering may be adjusted.

Additionally, each input may include a directionality input via which the user may specify whether each parameter is to be adjusted up, adjusted down, or adjusted either up or down. For example, as shown, rotation time may only be increased (e.g., relative to a default or specified rotation time of a set scan prescription), collimation may be increased or decreased, and pitch may only be increased. In some examples, the directionality of the respective adjustments may be set by the user; in other examples, the directionality of each adjustment may be fixed and the directionality inputs may visually indicate to the user the directionality in which the adjustments are to be made.

Thus, once the scan prescription for an adaptive scan protocol has been set (where the scan prescription includes a default or specified rotation time, collimation, and pitch) and the scan protocol is executed to scan a patient, the target table speed calculated by the adaptive scan protocol (as described above) may be reached by first adjusting a first parameter, in this example decreasing rotation time. Then, once a lower limit on the rotation time has been reached, if the target table speed is not achieved, a second parameter, herein collimation, may be adjusted (either increased or decreased). If the adjustment to the collimation does not cause the target table speed to be reached, a third parameter, such as pitch, may be increased. In this way, the user setting the adaptive scan protocol via the adaptive scan protocol GUI as described above with respect to FIG. 13 may indicate which imaging scan parameters are to be adjusted and in which order so that the target table speed can be reached while not compromising image quality.

FIG. 17 shows a second example portion 1700 of an adaptive scan protocol GUI. Portion 1700 includes the adaptive table speed input 1352. If a user selects or activates the adaptive table speed input 1352, additional inputs for setting the parameters for adjusting the table speed to reach the target table speed may be activated. As shown in FIG. 17, these additional inputs may include a first set of inputs 1702, a second set of inputs 1708, and a third set of inputs 1714. The first set of inputs 1702 may be specific to rotation time, so that a user may set how rotation time is to be adjusted to reach the target table speed. The first set of inputs 1702 includes an adjustment input 1704 and a value input 1706. The adjustment input 1704 may include a dropdown menu or other suitable input via which the user may specify if or how the rotation time is to be adjusted. The items available to be selected via the adjustment input 1704 may include less than or equal to, greater than or equal to, or equal to. If the user selects less than or equal to, the rotation time may be adjusted in order to reach the target table speed, but may not be adjusted beyond the value set in the value input 1706 (which in this example may be 0.6 s). Likewise, if the user selects greater than or equal to, the rotation time may be adjusted in order to reach the target table speed, but may not be adjusted to a value below the value set in the value input 1706. If the user selects equal to, the rotation time may be maintained at the value set in the value input 1706 and thus may not be adjusted to reach the target table speed.

The value input 1706 may include a dropdown menu via which a list of possible rotation time values (e.g., 0.5 s, 0.6 s, 0.7 s, etc.) is displayed and available for selection. In other examples, the value input 1706 may be configured to receive a keyboard or touchscreen input where the user is able to directly input any value (at least within a range of acceptable values) into the value input 1706.

The second set of inputs 1708 may be specific to collimation and may also include an adjustment input 1710 and a value input 1712. The adjustment input 1710 may include a menu similar to the adjustment input 1704, thereby allowing the user to specify whether or not collimation is to be adjusted, and if so, specify a lower limit or an upper limit for the collimation. The value input 1712 may include a dropdown menu showing a list of possible collimation values or may be configured to receive user input specifying a collimation value. In the example shown, collimation is set to be equal to 40 mm, and thus is not adjustable to reach the target table speed.

The third set of inputs 1714 may be specific to pitch and may also include an adjustment input 1716 and a value input 1718. The adjustment input 1716 may include a menu similar to the adjustment input 1704, thereby allowing the user to specify whether or not pitch is to be adjusted, and if so, specify a lower limit or an upper limit for the pitch. The value input 1718 may include a dropdown menu showing a list of possible pitch values available for selection, such as 1, 1.5, 1.375, etc.

Thus, once the scan prescription for an adaptive scan protocol has been set (where the scan prescription includes a default or specified rotation time, collimation, and pitch) and the scan protocol is executed to scan a patient, the target table speed calculated by the adaptive scan protocol (as described above) may be reached by adjusting rotation time, collimation, and/or pitch according to the constraints set by the user via the inputs shown in FIG. 17. For example, to reach a target table speed, rotation time may be adjusted (e.g., increased or decreased relative to the scan prescription value) but may be maintained under 0.6 s, collimation may not be adjusted, and pitch may be adjusted, but may be maintained under 1.0. In this way, the user setting the adaptive scan protocol via the adaptive scan protocol GUI as described above with respect to FIG. 13 may indicate which imaging scan parameters are to be adjusted and upper or lower limits for each parameter so that the target table speed can be reached while not compromising image quality.

Further, while the examples shown in FIGS. 16 and 17 show a set of inputs that may be presented for the user to select which parameter(s) is/are to be adjusted and in what manner, in some examples, the user may be presented with one or more inputs that allow the user to select image quality parameters, diagnostic goal of the scan, or other qualitative parameter, e.g., highest image quality vs. some sacrifice of image quality is acceptable, and the selected qualitative parameter(s) may be translated automatically into which scan parameters may be adjusted and by how much. In this way, user preference for the final images generated by the scan may be preserved while also lowering contrast agent volume, at least in some examples.

Thus, the systems and methods disclosed herein provide for estimating when various contrast agent time points/curves will occur for a specific patient, using a measured contrast enhancement curve as an input to a machine learning model to predict the remaining contrast agent time points or curves. The contrast enhancement curve may be a tissue uptake curve (TUC) measured at a tissue of interest (e.g., the brain), where the tissue is segmented in a plurality of images. In some examples, more than one contrast enhancement curve may be measured (e.g., the TUC may be measured and a short segment of an AIF curve may be measured). Based on these estimated time points, various contrast scan actions may be carried out. As explained above with respect to FIGS. 6A and 6B, the predicted time points may be used to adapt a CTA scan prescription.

The time points may be estimated from a TUC signal. As explained above with respect to FIGS. 3-5, the TUC signal may be a segment of a TUC measured at a segmented tissue region. The TUC signal may be robust to patient movement, given that the "ROI" is the segmented tissue and thus the ROI moves along with the patient from image to image. Further, the TUC signal may be measured at the head, rather than the neck, which may eliminate the need to adjust the imaging region of interest to go between the measurement of the TUC signal and diagnostic acquisitions (at least during the first contrast scan described herein).

In any of the methods described herein, once the time points have been estimated and the scan protocols adjusted (or not) based on the estimated time points, the AIF or TUC signal may continue to be measured in order to determine an actual AIF curve, VOF curve, and/or TUC. If an acquisition timed based on an estimated time point is determined to have been acquired at an incorrect time, an operator may be notified so that the acquisition may be repeated at the correct time. This may include performing an additional scan, with an additional contrast agent bolus, but may reduce undue reconstruction time, as the operator may be notified before full diagnostic reconstruction has begun, rather than waiting until the diagnostic images have been reconstructed to determine that one or more scans did not produce sufficient diagnostic images. Further, in any of the methods described herein, when the acquisitions are complete and as projection data is sent for image reconstruction/post-processing, the actual AIF/VOF/TUC curves may be generated and displayed to the user as comparison of the AIF/VOF/TUC estimates used to generate the scan prescription(s) described herein versus the actual measured AIF, VOF, and/or TUC curves. The differences between the estimated and measured AIF/VOF/TUC curves may be used to inform the user of the accuracy of the AIF/VOF/TUC estimates, inform the user of any errors in the estimates that might have impacted diagnostic image quality, and/or update the machine learning estimation models.

An embodiment relates to a method for an imaging system, including performing, with the imaging system, a first contrast scan of a subject including injection of a contrast agent to the subject; processing projection data of the subject acquired during the first contrast scan to measure a contrast signal of the subject at a monitoring area; estimating a target acquisition timing for a first acquisition of a second contrast scan of the subject based on the contrast signal; and performing, with the imaging system, the second contrast scan of the subject, with the first acquisition performed at the target acquisition timing and without performing any monitoring scans between the first contrast scan and the second contrast scan. In a first example of the method, estimating the target acquisition timing for the first acquisition of the second contrast scan of the subject based on the contrast signal comprises entering the contrast signal as input to a machine learning model trained to output the target acquisition timing as a function of the contrast signal. In a second example of the method, optionally including the first example, the injection of the contrast agent is a first injection of the contrast agent, wherein estimating the target acquisition timing comprises estimating an arterial peak timing of the contrast agent for a second injection of the contrast agent at a second region of the subject, different than the monitoring region, and wherein performing the second contrast scan of the subject with the first acquisition performed at the target acquisition timing comprises performing the second contrast scan including the second injection of the contrast agent, with the first acquisition performed at the arterial peak timing of the contrast agent for the second injection. In a third example of the method, optionally including one or both of the first and second examples, the second contrast scan is an angiography scan of a head and a neck of the subject, wherein the monitoring region comprises the head of the subject and the contrast signal comprises a tissue uptake curve of the head of the subject, and wherein the second region comprises an aortic arch of the subject. In a fourth example of the method, optionally including one or more or each of the first through third examples, the first contrast scan is a perfusion scan of the head of the subject and wherein performing the first contrast scan comprises performing one or more perfusion acquisitions with one or more parameters determined based on a monitoring scan performed prior to the one or more perfusion acquisitions, and wherein during the monitoring scan, the imaging system is placed into a different mode than during the one or more perfusion acquisitions and during the first acquisition. In a fifth example of the method, optionally including one or more or each of the first through fourth examples, the first acquisition spans a scan range, and further comprising determining a table velocity for moving a table supporting the subject during the first acquisition based on an estimated amount of time for the contrast agent of the second injection to flow across the scan range, and wherein performing the second contrast scan includes moving the table at the table velocity during the first acquisition. In a sixth example of the method, optionally including one or more or each of the first through fifth examples, the method further includes adjusting a contrast agent volume of the second injection based on the determined table velocity relative to a maximum table velocity and/or based on a confidence of the estimation of the amount of time for the contrast agent of the second injection to flow across the scan range. In a seventh example of the method, optionally including one or more or each of the first through sixth examples, moving the table at the determined table velocity includes adjusting one or more imaging system scan parameters to achieve the determined table velocity. In an eighth example of the method, optionally including one or more or each of the first through seventh examples, the one or more imaging system scan parameters include one or more of gantry rotation time, collimation, and pitch.

Another embodiment provides for a method for an imaging system, including: estimating, based on a contrast signal of a subject generated during a prior contrast scan of a head of the subject, a first contrast agent arterial peak timing at an aortic arch of the subject and a second contrast agent arterial peak timing at the head of the subject; setting a table velocity and a contrast agent injection volume based on an amount of time between the first contrast agent arterial peak timing and the second contrast agent arterial peak timing; commanding injection of a contrast agent to the subject at the contrast agent injection volume; initiating a contrast scan acquisition at the aortic arch of the subject at the estimated first contrast agent arterial peak timing; and moving a table supporting the subject during the contrast scan acquisition at the table velocity. In a first example of the method, the method further includes terminating the contrast scan acquisition after the second contrast agent arterial peak timing. In a second example of the method, optionally including the first example, setting the table velocity comprises setting the table velocity so that the table travels from a first position where the aortic arch is within an imaging region of the imaging system to a second position where the head is within the imaging region in the amount of time between the first contrast agent arterial peak timing and the second contrast agent arterial peak timing. In a third example of the method, optionally including one or both of the first and second examples, setting the contrast agent injection volume comprises: if the set table velocity is less than or equal to a maximum table velocity, setting the contrast agent injection volume to a minimum contrast agent injection volume; if the set table velocity is greater than the maximum table velocity, lowering the set table velocity and setting the contrast agent injection volume to a volume that is greater than the minimum contrast agent injection volume. In a fourth example of the method, optionally including one or more or each of the first through third examples, the table velocity is controlled according to rotation time, collimation, and/or pitch of the imaging system, and thereby moving the table at the table velocity comprises adjusting one or more of the rotation time, the collimation, and the pitch.

An embodiment relates to a system, including an x-ray source that emits x-rays toward a subject to be imaged; a detector that receives x-rays attenuated by the subject; a data acquisition system (DAS) operably connected to the detector; and a computer operably connected to the DAS and configured with instructions in non-transitory memory that when executed cause the computer to: process projection data of a monitoring region of interest (ROI) of the subject from the DAS to measure a contrast signal of a contrast agent in the subject; estimate a target acquisition timing for initiating a head and neck acquisition of a contrast scan of the subject based on the contrast signal; command injection of the contrast agent to the subject; and initiate the head and neck acquisition at the target acquisition timing, where the head and neck acquisition is the first acquisition that is performed after the injection of the contrast agent is commanded. In a first example of the system, the target acquisition timing is an arterial peak of the contrast agent at an aortic arch of the subject following the injection of the contrast agent. In a second example of the system, optionally including the first example, the non-transitory memory stores a machine learning model configured to estimate the target acquisition timing based on the contrast signal. In a third example of the system, optionally including one or both of the first and second examples, processing projection data of the monitoring ROI to measure the contrast signal comprises reconstructing a plurality of images from the projection data, segmenting a tissue of interest in each image of the plurality of images, measuring a signal intensity of the segmented tissue in each image relative to a baseline, and plotting each signal intensity as a function of time to generate the contrast signal. In a fourth example of the system, optionally including one or more or each of the first through third examples, the instructions, when executed, cause the computer to reconstruct one or more images from projection data from the DAS acquired during the head and neck acquisition. In a fifth example of the system, optionally including one or more or each of the first through third examples, the instructions, when executed, cause the computer to perform one or more additional acquisitions after the head and neck acquisitions.

In another representation, a method includes initiating a first contrast scan of a first subject; setting a first start time for a second contrast scan; processing acquired projection data of the first subject acquired during the first contrast scan to measure a first contrast signal of a contrast agent injected as part of the first contrast scan; identifying, based on the first contrast signal, an adaptive acquisition timing for a first acquisition of the second contrast scan before the first start time of the second contrast scan is reached, and in response, performing the second contrast scan according to an adaptive scan prescription; initiating a third contrast scan of a second subject; setting a second start time for a fourth contrast scan; processing acquired projection data of the second subject acquired during the third contrast scan to measure a second contrast signal of a contrast agent injected as part of the third contrast scan; identifying, based on the second contrast signal, that an adaptive acquisition timing for a first acquisition of the fourth contrast scan cannot be determined before the second start time of the fourth contrast scan is reached, and in response, performing the fourth contrast scan according to a fallback scan prescription. In a first example of the method, identifying, based on the first contrast signal, the adaptive acquisition timing before the first start time of the second contrast scan is reached comprises: evaluating the first contrast signal to determine if a peak is present in the first contrast signal; identifying the peak in the first contrast signal before the start time is reached; and entering the first contrast signal as input to a machine learning model trained to output the adaptive acquisition timing. In a second example of the method, optionally including the first example, identifying, based on the second contrast signal, that the adaptive acquisition timing for the first acquisition of the fourth contrast scan cannot be determined before the second start time of the fourth contrast scan is reached comprises evaluating the second contrast signal to determine if a peak is present in the second contrast signal; and not identifying the peak in the second contrast signal before the second start time is reached. In a third example of the method, optionally including one or both of the first and second examples, performing the fourth contrast scan according to the fallback scan prescription includes: commanding a second injection of the contrast agent; performing a monitoring scan following the commanding of the second injection; processing acquired projection data of the second subject acquired during the monitoring scan to generate a third contrast signal; and initiating a first acquisition of the fourth contrast scan at a timing determined based on the third contrast signal. In a fourth example of the method, optionally including one or more or each of the first through third examples, performing the second contrast scan according to the adaptive scan prescription includes: commanding a second injection of the contrast agent; and initiating a first acquisition of the second contrast scan at the adaptive acquisition timing, where the adaptive acquisition timing includes a time relative to the second injection when an arterial peak of the contrast agent of the second injection at an aortic arch of the first subject is estimated to occur. In a fifth example of the method, optionally including one or more or each of the first through fourth examples, performing the fourth contrast scan according to the fallback scan prescription further comprises commanding the second injection of a default volume of the contrast agent and moving a table supporting the second subject at a default speed during the first acquisition of the fourth contrast scan. In a sixth example of the method, optionally including one or more or each of the first through fifth examples, performing the second contrast scan according to the adaptive scan prescription further comprises commanding the second injection of an adaptive volume of the contrast agent and moving a table supporting the first subject at an adaptive speed during the first acquisition of the second contrast scan, where the adaptive speed is determined based on an estimated amount of time for the contrast agent of the second injection to flow across a scan range of the first acquisition of the second contrast scan.

In another representation, a method includes initiating a first contrast scan of a subject; setting a start time for a second contrast scan to be performed after the first contrast scan according to a fallback scan prescription; processing acquired projection data of the subject acquired during the first contrast scan to measure a contrast signal of a contrast agent injected as part of the first contrast scan; and responsive to identifying, based on the contrast signal, an adaptive acquisition timing for a first acquisition of the second contrast scan before the start time of the second contrast scan is reached, performing the second contrast scan according to an adaptive scan prescription, otherwise performing the second contrast scan according to the fallback scan prescription. In a first example of the method, identifying, based on the contrast signal, the adaptive acquisition timing before the start time of the second contrast scan is reached comprises: evaluating the contrast signal to determine if a peak is present in the contrast signal; if the peak in the contrast signal is identified before the start time is reached, entering the contrast signal as input to a machine learning model trained to output the adaptive acquisition timing; and if the peak in the contrast signal is not identified before the start time is reached, indicating that the adaptive acquisition timing cannot be determined and performing the second contrast scan according to the fallback scan prescription. In a second example of the method, optionally including the first example, performing the second contrast scan according to the fallback scan prescription includes: commanding a second injection of the contrast agent; performing a monitoring scan following the commanding of the second injection; processing acquired projection data of the subject acquired during the monitoring scan to generate a second contrast signal; and initiating the first acquisition at a timing determined based on the second contrast signal. In a third example of the method, optionally including one or both of the first and second examples, performing the second contrast scan according to the adaptive scan prescription includes: commanding the second injection of the contrast agent; and initiating the first acquisition at the adaptive acquisition timing, where the adaptive acquisition timing includes a time relative to the second injection when an arterial peak of the contrast agent of the second injection at an aortic arch of the subject is estimated to occur. In a fourth example of the method, optionally including one or more or each of the first through third examples, performing the second contrast scan according to the fallback scan prescription further comprises commanding the second injection of a default volume of the contrast agent and moving a table supporting the subject at a default speed during the first acquisition. In a fifth example of the method, optionally including one or more or each of the first through fourth examples, performing the second contrast scan according to the adaptive scan prescription further comprises commanding the second injection of an adaptive volume of the contrast agent and moving the table supporting the subject at an adaptive speed during the first acquisition, where the adaptive speed is determined based on an estimated amount of time for the contrast agent of the second injection to flow across a scan range of the first acquisition. In a sixth example of the method, optionally including one or more or each of the first through fifth examples, the default speed is determined based on scan parameters defined by the fallback scan prescription, the scan parameters including one or more of rotation time, collimation, and pitch, and further comprising moving the table at the adaptive speed during the first acquisition when performing the second contrast scan according to the adaptive scan prescription by adjusting one or more of the scan parameters. In a seventh example of the method, optionally including one or more or each of the first through sixth examples, processing the acquired projection data to measure the contrast signal comprises reconstructing a plurality of images from the projection data, segmenting a tissue of interest in each image of the plurality of images, measuring a signal intensity of the segmented tissue in each image relative to a baseline, and plotting each signal intensity as a function of time to generate the contrast signal. In an eighth example of the method, optionally including one or more or each of the first through seventh examples, the first contrast scan is a perfusion scan, wherein the tissue of interest is a brain of the subject, and wherein the second contrast scan is an angiography scan.

In another representation, a method for an imaging system includes during a first contrast scan of a subject with the imaging system, measuring a contrast level of a first contrast bolus of the subject to generate a contrast signal, the first contrast bolus delivered to the subject via a first injection; setting a start time for a second injection of a second contrast bolus to the subject; if a peak in the contrast signal is not identified before the start time of the second injection, commanding initiation of the second injection at the start time and carrying out a second contrast scan according to a fallback scan prescription that includes generating a second contrast signal and initiating a head and neck acquisition of the second contrast scan at a timing based on the second contrast signal; and if the peak in the contrast signal is identified before the start time of the second injection, commanding initiation of the second injection and carrying out the second contrast scan according to an adaptive scan prescription that includes initiating the head and neck acquisition of the second contrast scan at a timing based on the first contrast signal, without generating the second contrast signal. In a second example of the method, optionally including the first example, carrying out the second contrast scan according to the fallback scan prescription further comprises commanding initiation of the second injection of the second contrast bolus having a default volume and moving a table supporting the subject at a default speed during the head and neck acquisition, wherein the default speed is determined based on scan parameters defined by the fallback scan prescription, the scan parameters including one or more of rotation time, collimation, and pitch. In a third example of the method, optionally including one or both of the first and second examples, carrying out the second contrast scan according to the adaptive scan prescription comprises commanding initiation of the second injection of the second contrast bolus having an adaptive volume and moving a table supporting the subject at an adaptive speed during the head and neck acquisition, the adaptive speed determined based on an estimated amount of time for the second contrast bolus to flow across a scan range of the head and neck acquisition. In a fourth example of the method, optionally including one or more or each of the first through third examples, the fallback scan prescription defines a rotation time, a collimation, and a pitch for carrying out the second contrast scan, and further comprising adjusting one or more of the rotation time, the collimation, and the pitch to move the table at the adaptive speed. In a fifth example of the method, optionally including one or more or each of the first through fourth examples, initiating the head and neck acquisition of the second contrast scan at the timing based on the first contrast signal comprises determining the timing based on output from a machine learning model. In a sixth example of the method, optionally including one or more or each of the first through fifth examples, determining the timing comprises determining an amount of elapsed time, relative to initiation of the second injection, that an arterial peak of the second contrast bolus at an aortic arch of the subject is going to occur, and after commanding initiation of the second injection, initiating the head and neck acquisition of the second contrast scan after the amount of elapsed time.

In another representation, a system includes an x-ray source that emits a beam of x-rays toward a subject to be imaged; a detector that receives x-rays attenuated by the subject; a data acquisition system (DAS) operably connected to the detector; and a computer operably connected to the DAS and configured with instructions in non-transitory memory that when executed cause the computer to: initiate a first contrast scan of the subject; set a start time for a second contrast scan to be performed after the first contrast scan according to a fallback scan prescription; process acquired projection data of the subject acquired during the first contrast scan to measure a contrast signal of a contrast agent injected via a first injection as part of the first contrast scan; and responsive to identifying, based on the contrast signal, an adaptive acquisition timing for a first acquisition of the second contrast scan before the start time of the second contrast scan is reached, perform the second contrast scan according to an adaptive scan prescription, otherwise perform the second contrast scan according to the fallback scan prescription. In a second example of the system, optionally including the first example, the non-transitory memory stores a machine learning model configured to determine the adaptive acquisition timing based on the contrast signal. In a third example of the system, optionally including one or both of the first and second examples, performing the second contrast scan according to the fallback scan prescription includes: commanding a second injection of the contrast agent; performing a monitoring scan following the commanding of the injection; processing acquired projection data of the subject acquired during the monitoring scan to generate a second contrast signal; and initiating the first acquisition at a timing determined based on the second contrast signal. In a fourth example of the system, optionally including one or more or each of the first through third examples, performing the second contrast scan according to the adaptive scan prescription includes: commanding the second injection of the contrast agent; and initiating the first acquisition at the adaptive acquisition timing, where the adaptive acquisition timing includes a time relative to the second injection when an arterial peak of the contrast agent at an aortic arch of the subject is estimated to occur. In a fifth example of the system, optionally including one or more or each of the first through fourth examples, the contrast signal comprises a contrast level of the subject over time measured at a head of the subject.

In another representation, a method for a computing device communicatively coupled to an imaging system includes displaying an adaptive scan protocol graphical user interface (GUI) on a display device coupled to the computing device; setting one or more parameters of an adaptive contrast scan protocol in response to user input to the adaptive scan protocol GUI, where the adaptive contrast scan protocol includes a second contrast scan following a first contrast scan, and where the one or more parameters include a delay for the second contrast scan that is determined, during execution of the adaptive contrast scan protocol on a subject, based on a contrast signal measured as part of the first contrast scan, the delay including an amount of time between injection of a contrast agent to the subject for the second contrast scan and initiation of a first diagnostic acquisition of the second contrast scan; and storing the adaptive contrast scan protocol in memory of the computing device. In a first example of the method, setting the one or more parameters further includes selecting, via user input to the adaptive scan protocol GUI, a fixed timing or a personalized timing for the injection of the contrast agent, wherein responsive to the personalized timing being selected and during the execution of the adaptive contrast scan protocol on the subject, the injection of the contrast agent is performed at the personalized timing relative to the first contrast scan, and wherein the personalized timing is determined based on the contrast signal. In a second example of the method, optionally including the first example, setting the one or more parameters further includes setting a range of contrast agent volumes for the injection of the contrast agent via user input to the adaptive scan protocol GUI. In a third example of the method, optionally including one or both of the first and second examples, during execution of the adaptive contrast scan protocol on the subject, a contrast agent volume is selected from the range of contrast agent volumes based at least in part on the contrast signal. In a fourth example of the method, optionally including one or more or each of the first through third examples, setting the one or more parameters further includes setting a table speed of a table supporting the subject during the first diagnostic acquisition. In a fifth example of the method, optionally including one or more or each of the first through fourth examples, setting the table speed includes setting the table speed to a determined contrast travel time between a start location and an end location of the first diagnostic acquisition. In a sixth example of the method, optionally including one or more or each of the first through fifth examples, the first contrast scan is a perfusion scan and the second contrast scan in an angiography scan and wherein the first diagnostic acquisition is a head and neck acquisition commencing at a base of a neck of the subject and terminating at a top of a head of the subject. In a seventh example of the method, optionally including one or more or each of the first through sixth examples, the adaptive contrast scan protocol is configured to be carried out when an acute stroke is suspected or confirmed in the subject. In an eighth example of the method, optionally including one or more or each of the first through seventh examples, the delay for the second contrast scan is an adaptive delay and the contrast signal is a first contrast signal, the adaptive scan protocol further includes a fallback delay, during execution of the adaptive scan protocol on the subject in a first mode, the first diagnostic acquisition is initiated after the adaptive delay, and during execution of the adaptive scan protocol on the subject in a second mode, the first diagnostic acquisition is initiated after the fallback delay, the fallback delay determined based on a second contrast signal measured after the injection of the contrast agent. In a ninth example of the method, optionally including one or more or each of the first through eighth examples, the first mode comprises the first contrast signal including an identifiable arterial peak, venous peak, or tissue uptake peak, and wherein the second mode comprises the first contrast signal lacking an identifiable arterial peak, venous peak, or tissue uptake peak.

In another representation, a method for a computing device communicatively coupled to an imaging system includes setting an adaptive scan prescription and a fallback scan prescription for a second contrast scan for imaging a patient with the imaging system based on an adaptive scan protocol, the second contrast scan following a first contrast scan of the patient; displaying, on a display device coupled to the computing device, a run-time graphical user interface (GUI), the run-time GUI including a visual representation of the adaptive scan protocol; during the first contrast scan, measuring a contrast signal of the patient; responsive to a peak in the contrast signal being identified before a start time of the second contrast scan, executing the second contrast scan according to the adaptive scan prescription and updating the run-time GUI to display an adaptive prep delay comprising an amount of time between injection of a contrast agent for the second contrast scan and initiation of a first diagnostic acquisition of the second contrast scan that is determined based on the contrast signal; and responsive to the peak in the contrast signal not being identified before the start time of the second contrast scan, executing the second contrast scan according to the fallback scan prescription. In a first example of the method, executing the second contrast scan according to the fallback scan prescription includes updating the run-time GUI to display a prompt for the user to perform a monitoring scan, performing the monitoring scan after commanding the injection of the contrast agent for the second contrast scan, measuring a second contrast signal of the patient during the monitoring scan, and initiating the first diagnostic acquisition at a timing determined based on the second contrast signal. In a second example of the method, optionally including the first example, performing the monitoring scan includes performing one or more non-diagnostic acquisitions, the one or more non-diagnostic acquisitions performed before the first diagnostic acquisition. In a third example of the method, optionally including one or both of the first and second examples, executing the second contrast scan according to the adaptive scan prescription includes commanding the injection of the contrast agent for the second contrast scan and initiating the first diagnostic acquisition after the adaptive prep delay has elapsed, where the first diagnostic acquisition is a first acquisition of the second contrast scan performed by the imaging system after the commanding of the injection of the contrast agent for the second contrast scan.

In another representation, a system includes a display device; a non-transitory memory storing instructions; and a processor configured to execute the instructions to: display, on the display device, an adaptive scan protocol graphical user interface (GUI); adjust one or more adaptive scan parameters of a scan protocol in response to user input to the adaptive scan protocol GUI to generate an adapted scan protocol that includes a first contrast scan followed by a second contrast scan; store the adapted scan protocol in the non-transitory memory; responsive to a user request, execute the adapted scan protocol to image a patient, where executing the adjusted scan protocol comprises: displaying, on the display device, a run-time GUI including a visual representation of the adapted scan protocol, performing, via an imaging system, one or more acquisitions according to the adjusted scan protocol after a first contrast injection has commenced to carry out the first contrast scan, measuring a contrast level curve of the patient based on projection data acquired via the one or more acquisitions, updating the run-time GUI to display an adaptive prep delay calculated based on the contrast level curve, the adaptive prep delay comprising an amount of time between a second contrast injection for the second contrast scan and initiation of a first diagnostic acquisition of the second contrast scan, and after the second contrast injection has commenced, initiating, via the imaging system, the first diagnostic acquisition of the second contrast scan once the adaptive prep delay has elapsed. In a first example of the system, the imaging system is a computed tomography imaging system, wherein the first contrast scan is a perfusion scan of a head of the patient, and wherein the second contrast scan is an angiography scan of a neck and the head of the patient. In a second example of the system, optionally including the first example, the non-transitory memory stores a machine learning model trained to receive the contrast level curve as input and wherein the adaptive prep delay is calculated based on output from the machine learning model. In a third example of the system, optionally including one or both of the first and second examples, adjusting one or more adaptive scan parameters of the scan protocol in response to user input to the adaptive scan protocol GUI to generate the adapted scan protocol comprises adjusting a table speed of a table adapted to support the patient from a fixed table speed to an adaptive table speed, the adaptive table speed adjusted during execution of the adapted scan protocol based on the contrast level curve. In a fourth example of the system, optionally including one or more or each of the first through third examples, adjusting one or more adaptive scan parameters of the scan protocol in response to user input to the adaptive scan protocol GUI to generate the adapted scan protocol comprises adjusting a contrast volume of the second contrast injection from a fixed volume to an adaptive volume, the adaptive volume adjusted during execution of the adapted scan protocol based on the contrast level curve. In a fifth example of the system, optionally including one or more or each of the first through fourth examples, executing the adjusted scan protocol further comprises reconstructing one or more images from projection data acquired during the first diagnostic acquisition.

In another representation, a method includes setting, via user input to an adaptive contrast scan protocol GUI, a fallback scan prescription that includes a rotation time, a collimation, and a pitch to be applied to an imaging system while imaging a patient in a first mode, where the rotation time, the collimation, and the pitch of the fallback scan prescription result in a first table speed of a table supporting the patient; setting, via user input to the adaptive contrast scan protocol GUI, one or more adjustments to the rotation time, the collimation, and the pitch that can be applied to the imaging system while imaging the patient in a second mode according to an adaptive scan prescription if a target table speed does not match the first table speed; determining, prior to the imaging of the patient, that the patient is going to be imaged in the first mode or in the second mode; if the patient is imaged in the first mode, applying the rotation time, the collimation, and the pitch of the fallback scan prescription to the imaging system and moving the patient during a first acquisition at the first table speed; if the patient is imaged in the second mode and the target speed does not match the first table speed, adjusting one or more of the rotation time, the collimation, and the pitch according to the adaptive scan prescription, applying the adjusted rotation time, the collimation, and the pitch to the imaging system, and moving the patient during the first acquisition at a second table speed. In some examples, the second table speed is equal to the target table speed. In other examples, the second table speed is closer to the target table speed than the first target table speed.

A technical effect of the disclosure is that an adaptive, personalized contrast scan may be performed using a contrast signal generated during a prior contrast scan, which may increase diagnostic image quality and/or reduce patient radiation exposure, without compromising scan quality for patients whose contrast agent kinetics cannot be reasonable estimated within the time frame of the scan protocol. A further technical effect of the disclosure is that scan durations may be reduced and subsequent patient treatment decisions may be more accurate, reducing unnecessary transfers to other medical facilities and improving patient outcomes.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an imaging system, comprising:
  performing, with the imaging system, a first contrast scan of a subject, the first contrast scan including a first injection of a contrast agent to the subject;
  processing projection data of the subject acquired during the first contrast scan to measure a contrast signal of the subject at a monitoring area;

estimating a target acquisition timing for a first acquisition of a second contrast scan of the subject based on the contrast signal, the target acquisition timing comprising an arterial peak timing of the contrast agent for a second injection of the contrast agent, the arterial peak timing at a second region of the subject, different than the monitoring area; and upon the second injection of the contrast agent, performing, with the imaging system, the second contrast scan of the subject, with the first acquisition performed at the arterial peak timing of the contrast agent for the second injection and without performing any monitoring scans between the first contrast scan and the second contrast scan.

2. The method of claim 1, wherein estimating the target acquisition timing for the first acquisition of the second contrast scan of the subject based on the contrast signal comprises entering the contrast signal as input to a machine learning model trained to output the target acquisition timing as a function of the contrast signal.

3. The method of claim 1, wherein the second contrast scan is an angiography scan of a head and a neck of the subject, wherein the monitoring area comprises the head of the subject and the contrast signal comprises a tissue uptake curve of the head of the subject, and wherein the second region comprises an aortic arch of the subject.

4. The method of claim 3, wherein the first contrast scan is a perfusion scan of the head of the subject and wherein performing the first contrast scan comprises performing one or more perfusion acquisitions with one or more parameters determined based on a monitoring scan performed prior to the one or more perfusion acquisitions, and wherein during the monitoring scan, the imaging system is placed into a different mode than during the one or more perfusion acquisitions and during the first acquisition.

5. The method of claim 1, wherein the first acquisition spans a scan range, and further comprising determining a table velocity for moving a table supporting the subject during the first acquisition based on an estimated amount of time for the contrast agent of the second injection to flow across the scan range, and wherein performing the second contrast scan includes moving the table at the table velocity during the first acquisition.

6. The method of claim 5, further comprising adjusting a contrast agent volume of the second injection based on the table velocity relative to a maximum table velocity and/or based on a confidence of the estimated amount of time for the contrast agent of the second injection to flow across the scan range.

7. The method of claim 5, wherein moving the table at the table velocity includes adjusting one or more imaging system scan parameters to achieve the table velocity.

8. The method of claim 7, wherein the one or more imaging system scan parameters include one or more of gantry rotation time, collimation, and pitch.

9. The method of claim 1, further comprising estimating a head arterial inflow (AIF) curve from the contrast signal and determining the arterial peak timing at the second region as a function of an arterial peak and an arterial ascent knee of the head AIF curve.

10. A method for an imaging system, comprising:
estimating, based on a contrast signal of a subject generated during a prior contrast scan of a head of the subject, a first contrast agent arterial peak timing at an aortic arch of the subject and a second contrast agent arterial peak timing at the head of the subject;

setting a table velocity and a contrast agent injection volume based on an amount of time between the first contrast agent arterial peak timing and the second contrast agent arterial peak timing;
commanding injection of a contrast agent to the subject at the contrast agent injection volume;
initiating a contrast scan acquisition at the aortic arch of the subject at the first contrast agent arterial peak timing; and
moving a table supporting the subject during the contrast scan acquisition at the table velocity.

11. The method of claim 10, further comprising terminating the contrast scan acquisition after the second contrast agent arterial peak timing, and wherein commanding injection of the contrast agent comprises commanding injection of the contrast agent at an estimated venous return to baseline of a prior contrast injection performed as part of the prior contrast scan.

12. The method of claim 10, wherein setting the table velocity comprises setting the table velocity so that during the contrast scan acquisition, the table travels from a first position where the aortic arch is within an imaging region of the imaging system to a second position where the head is within the imaging region in the amount of time between the first contrast agent arterial peak timing and the second contrast agent arterial peak timing.

13. The method of claim 12, wherein setting the contrast agent injection volume comprises:
if the set table velocity is less than or equal to a maximum table velocity, setting the contrast agent injection volume to a minimum contrast agent injection volume; and
if the set table velocity is greater than the maximum table velocity, lowering the set table velocity and setting the contrast agent injection volume to a volume that is greater than the minimum contrast agent injection volume.

14. The method of claim 12, wherein the table velocity is controlled according to rotation time, collimation, and/or pitch of the imaging system, and thereby moving the table at the table velocity comprises adjusting one or more of the rotation time, the collimation, and the pitch.

15. A system, comprising:
an x-ray source that emits x-rays toward a subject to be imaged;
a detector that receives x-rays attenuated by the subject;
a data acquisition system (DAS) operably connected to the detector; and
a computer operably connected to the DAS and configured with instructions in non-transitory memory that when executed cause the computer to:
process projection data of a monitoring region of interest (ROI) of the subject from the DAS to measure a contrast signal of a contrast agent in the subject, the projection data acquired during a first contrast scan;
estimate a target acquisition timing for initiating a head and neck acquisition of a second contrast scan of the subject based on the contrast signal;
command injection of the contrast agent to the subject; and
initiate the head and neck acquisition at the target acquisition timing, wherein the head and neck acquisition is a first acquisition in time that is performed after the injection of the contrast agent is commanded.

16. The system of claim 15, wherein the target acquisition timing is an arterial peak of the contrast agent at an aortic arch of the subject following the injection of the contrast agent.

17. The system of claim 15, wherein the non-transitory memory stores a machine learning model configured to estimate the target acquisition timing based on the contrast signal.

18. The system of claim 15, wherein processing projection data of the monitoring ROI to measure the contrast signal comprises reconstructing a plurality of images from the projection data, segmenting a tissue of interest in each image of the plurality of images, measuring a signal intensity of the segmented tissue of interest in each image relative to a baseline, and plotting each signal intensity as a function of time to generate the contrast signal.

19. The system of claim 15, wherein the instructions, when executed, cause the computer to reconstruct one or more images from the projection data from the DAS acquired during the head and neck acquisition.

20. The system of claim 15, wherein the first contrast scan is a perfusion scan and the second contrast scan is an angiography scan that includes the head and neck acquisition, wherein the instructions, when executed, cause the computer to perform one or more additional angiography acquisitions after the head and neck acquisition, and wherein only angiography acquisitions are performed following the injection of the contrast agent.

* * * * *